United States Patent
Miyamoto et al.

(10) Patent No.: US 10,920,704 B2
(45) Date of Patent: Feb. 16, 2021

(54) ABNORMALITY DIAGNOSIS SYSTEM OF AIR-FUEL RATIO SENSOR

(71) Applicant: TOYOTA JIDOSHA KABUSHIKI KAISHA, Toyota (JP)

(72) Inventors: Hiroshi Miyamoto, Susono (JP); Toru Kidokoro, Hadano (JP); Yasushi Iwazaki, Ebina (JP); Kenji Suzuki, Gotemba (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 15/537,194

(22) PCT Filed: Nov. 9, 2015

(86) PCT No.: PCT/JP2015/005594
§ 371 (c)(1),
(2) Date: Jun. 16, 2017

(87) PCT Pub. No.: WO2016/098276
PCT Pub. Date: Jun. 23, 2016

(65) Prior Publication Data
US 2017/0342927 A1  Nov. 30, 2017

(30) Foreign Application Priority Data

Dec. 19, 2014 (JP) .............. JP2014-257873

(51) Int. Cl.
*F02D 41/14* (2006.01)
*F02D 41/12* (2006.01)
(Continued)

(52) U.S. Cl.
CPC ......... *F02D 41/1495* (2013.01); *F01M 13/00* (2013.01); *F02D 41/123* (2013.01);
(Continued)

(58) Field of Classification Search
CPC .. F02D 41/1495; F02D 41/123; F02D 41/222; F02D 2041/224; F02D 2250/08;
(Continued)

(56) References Cited

U.S. PATENT DOCUMENTS 4,278,060 A * 7/1981 Isobe .................. F02D 41/1479
123/437
5,178,121 A * 1/1993 Kitajima ............. F02D 19/0631
123/689

(Continued)

FOREIGN PATENT DOCUMENTS

JP  2002-243694 A  8/2002
JP  2007-127076 A  5/2007
(Continued)

OTHER PUBLICATIONS

Lampton, How does a positive crankcase ventilation (PCV system work?), Aug. 14, 2012 [retrieved on Aug. 5, 2019]. Retrieved from the Internet: <URL: https://web.archive.org/web/20120814114740/ https://auto.howstuffworks.com/positive-crankcase-ventilation-system. htm> (Year: 2012).*

*Primary Examiner* — Alexander Satanovsky
*Assistant Examiner* — Liam R Casey
(74) *Attorney, Agent, or Firm* — Hunton Andrews Kurth LLP

(57) ABSTRACT

An abnormality diagnosis system of an air-fuel ratio sensor acquires a blowby gas flow ratio showing a ratio of the flow of blowby gas to the flow of gas to a combustion chamber and an output current of an air-fuel ratio sensor during fuel cut control in which an internal combustion engine stops the feed of fuel to the combustion chamber and at a plurality of points of time of different flows of blowby gas passing through a blowby gas passage and flowing to the downstream side of a throttle valve in the intake passage, calculate an output current of the air-fuel ratio sensor corresponding (Continued)

to a blowby gas flow ratio smaller than the blowby gas flow ratios acquired at the plurality of points of time, based on the acquired blowby gas flow ratio and output current, and judge the air-fuel ratio sensor for abnormality based on the calculated output current.

6 Claims, 21 Drawing Sheets

(51) Int. Cl.
    *F02D 41/22*     (2006.01)
    *F01M 13/00*     (2006.01)
    *G01N 33/00*     (2006.01)
    *F02D 41/24*     (2006.01)

(52) U.S. Cl.
    CPC ....... *F02D 41/222* (2013.01); *F02D 41/2416* (2013.01); *G01N 33/007* (2013.01); *F02D 2041/224* (2013.01); *F02D 2250/08* (2013.01)

(58) Field of Classification Search
    CPC ... F02D 41/2416; F01M 13/00; G01N 33/007
    See application file for complete search history.

(56) References Cited

U.S. PATENT DOCUMENTS

| | | | |
|---|---|---|---|
| 9,255,533 B2* | 2/2016 | Viehover | F01M 13/00 |
| 2002/0022921 A1* | 2/2002 | Nakagawa | F02D 41/008 |
| | | | 701/109 |
| 2002/0129802 A1* | 9/2002 | Hayashi | F02D 41/0032 |
| | | | 123/698 |
| 2008/0040018 A1* | 2/2008 | Katoch | F02D 41/22 |
| | | | 701/103 |
| 2008/0262704 A1* | 10/2008 | Kawase | F01N 9/00 |
| | | | 701/109 |
| 2009/0230761 A1* | 9/2009 | Sekiguchi | B60T 8/442 |
| | | | 303/2 |
| 2010/0076635 A1* | 3/2010 | Sugimoto | B60K 6/445 |
| | | | 701/22 |
| 2010/0083937 A1 | 4/2010 | Tsunooka et al. | |
| 2010/0163008 A1* | 7/2010 | Kato | F02D 41/1458 |
| | | | 123/674 |
| 2011/0290217 A1* | 12/2011 | Kimura | F02D 41/221 |
| | | | 123/48 C |
| 2011/0313642 A1* | 12/2011 | Sano | F02D 13/06 |
| | | | 701/104 |
| 2013/0019651 A1* | 1/2013 | Sasaki | F02D 41/222 |
| | | | 73/1.02 |
| 2014/0020363 A1* | 1/2014 | Sasaki | F01N 3/10 |
| | | | 60/274 |
| 2014/0046573 A1* | 2/2014 | Maemura | F02D 41/1495 |
| | | | 701/102 |
| 2015/0101328 A1* | 4/2015 | Surnilla | F02M 35/10222 |
| | | | 60/599 |
| 2016/0202210 A1* | 7/2016 | Nakata | G01N 27/4065 |
| | | | 204/401 |
| 2016/0223488 A1* | 8/2016 | Kayama | G01N 27/4175 |

FOREIGN PATENT DOCUMENTS

| | | |
|---|---|---|
| JP | 2010-174790 A | 8/2010 |
| JP | 2011-226351 A | 11/2011 |
| JP | 2012-026428 A | 2/2012 |
| JP | 2012-031869 A | 2/2012 |
| JP | 2012-072686 A | 4/2012 |
| JP | 2012-145041 A | 8/2012 |
| JP | 2013-072343 A | 4/2013 |
| JP | 2013-083203 A | 5/2013 |
| JP | 2014-101863 A | 6/2014 |

* cited by examiner

FIG. 7
[Fig. 7A]
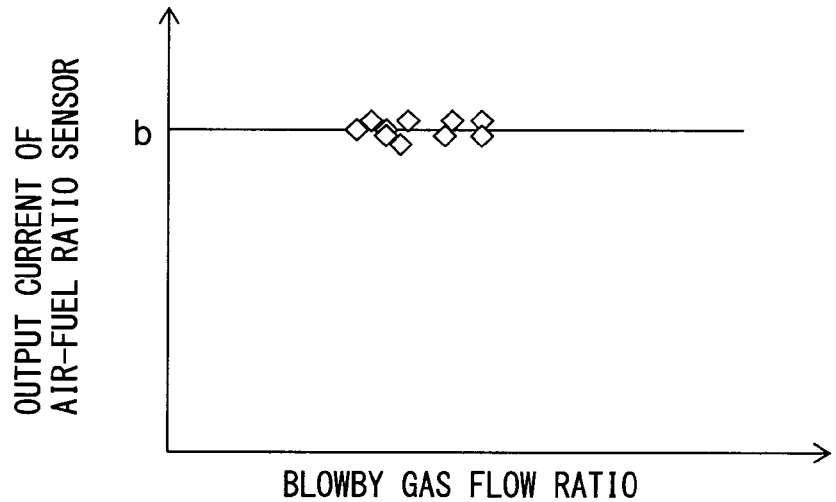
[Fig. 7B]
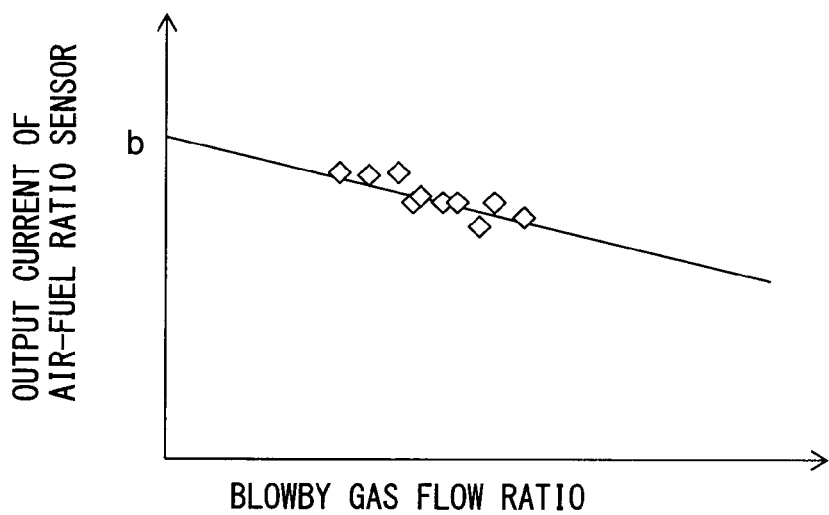
[Fig. 7C]
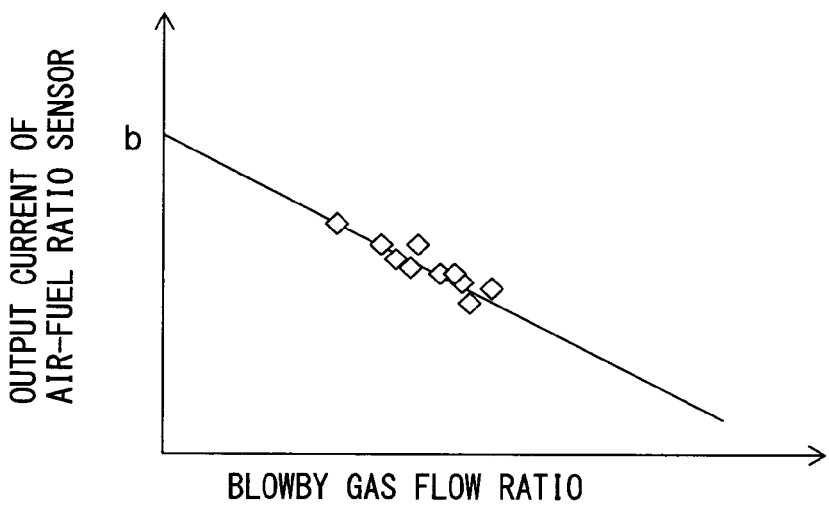

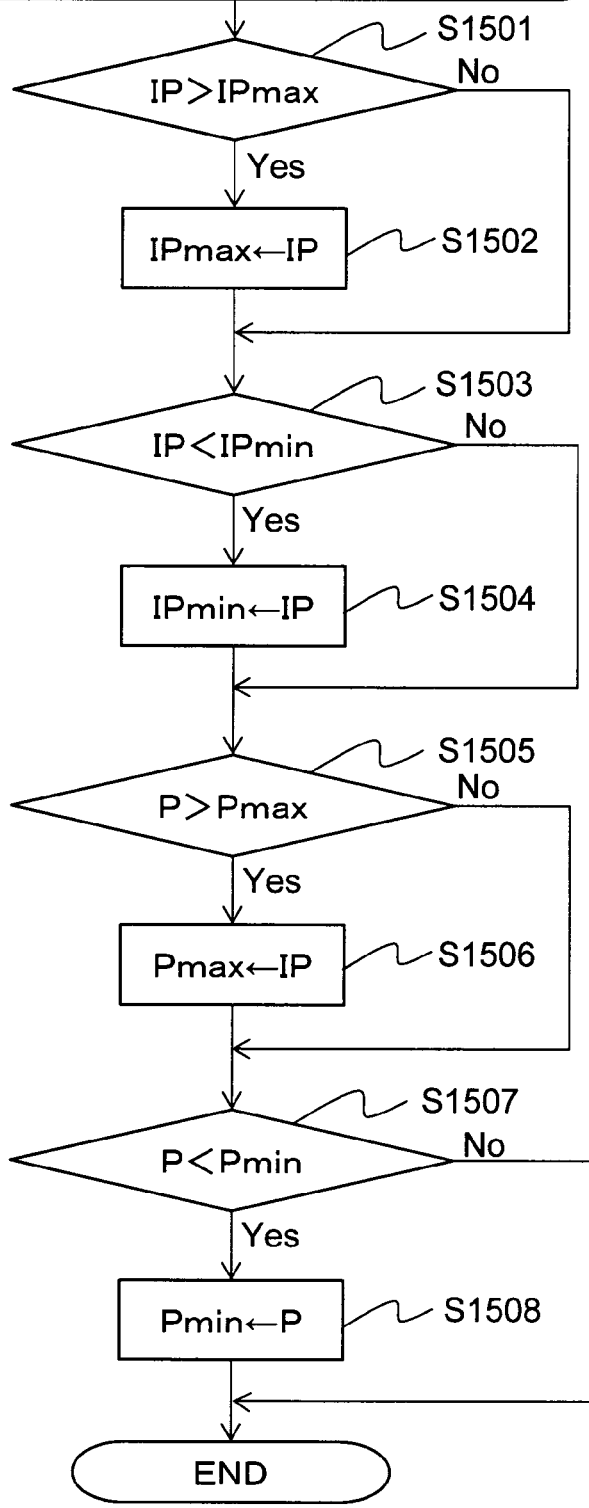

ABNORMALITY DIAGNOSIS SYSTEM OF AIR-FUEL RATIO SENSOR

CROSS-REFERENCE TO RELATED APPLICATIONS

This is a national phase application based on the PCT International Patent Application No. PCT/JP2015/005594 filed Nov. 9, 2015, claiming priority to Japanese Patent Application No. 2014-257873 filed Dec. 19, 2014, the entire contents of both of which are incorporated herein by reference.

TECHNICAL FIELD

The invention relates to an abnormality diagnosis system of an air-fuel ratio sensor.

BACKGROUND ART

Known in the past has been an internal combustion engine which provides an air-fuel ratio sensor in an exhaust passage of the internal combustion engine and controls the amount of fuel fed to a combustion chamber of the internal combustion engine based on the output of this air-fuel ratio sensor.

As one example of an air-fuel ratio sensor, there is known an air-fuel ratio sensor which changes in output current linearly (proportionally) to an exhaust air-fuel ratio (for example, PTL 1). The output current becomes larger the higher the exhaust air-fuel ratio (the leaner it becomes). For this reason, by detecting the output current of the air-fuel ratio sensor, it is possible to estimate the exhaust air-fuel ratio.

However, such an air-fuel ratio sensor gradually deteriorates along with use and sometimes changes in gain characteristics. If the gain characteristics change, the output current of the air-fuel ratio sensor becomes too large or too small for the exhaust air-fuel ratio. As a result, the exhaust air-fuel ratio is mistakenly estimated, and therefore the various types of control carried out by a control device of the internal combustion end up being obstructed.

Therefore, PTL 2 proposes an abnormality diagnosis system which diagnoses abnormality in an air-fuel ratio sensor. In such an abnormality diagnosis system, during fuel cut control wherein the internal combustion engine stops the feed of fuel to the combustion chambers, diagnosis of abnormality of the air-fuel ratio sensor is carried out based on the value of the applied voltage of the air-fuel ratio sensor. According to PTL 2, during fuel cut control, the exhaust air-fuel ratio is constant and can be recognized, and therefore it is possible to accurately diagnose abnormality of an air-fuel ratio sensor without being influenced by fluctuations in the exhaust air-fuel ratio.

CITATION LIST

Patent Literature

PTL 1: Japanese Patent Publication No. 2002-243694A
PTL 2: Japanese Patent Publication No. 2010-174790A
PTL 3: Japanese Patent Publication No. 2014-101863A
PTL 4: Japanese Patent Publication No. 2007-127076A

SUMMARY OF INVENTION

Technical Problem

In this regard, in an internal combustion engine, air-fuel mixture leaks out from a clearance between a piston and a cylinder block to the inside of a crankcase, that is, "blowby gas" is generated. If the blowby gas remains inside the crankcase, it will cause deterioration of the engine oil, corrosion of metal, air pollution, etc. Therefore, an internal combustion engine is provided with a blowby gas passage which connects the crankcase and the intake passage. The blowby gas passes through the blowby gas passage to be returned to the intake passage and is burned together with the new air-fuel mixture.

Further, in a cylinder injection type internal combustion engine which directly injects fuel into a combustion chamber, the distance between an injection port of a fuel injector and a cylinder wall surface is extremely short, and therefore the injected fuel directly strikes the cylinder wall surface. At the time of cold startup, the fuel deposited at the cylinder wall does not easily vaporize, and therefore it leaks out from the clearance between the piston and cylinder into the crankcase and is mixed with the engine oil. On the other hand, after the internal combustion engine is warmed up, the temperature of the engine oil also rises, and therefore the fuel content in the engine oil vaporizes. Therefore, at the time of cold startup, if the internal combustion engine is warmed up while the amount of fuel which is contained in engine oil is small, the fuel content in the blowby gas will not increase much at all.

However, if an operating state where the internal combustion engine is started at a low temperature and is stopped in a shorter time than the time by which the internal combustion engine is warmed up, a so-called "short trip", is repeated, the amount of fuel content in the engine oil will increase. After that, if the internal combustion engine is warmed up, the large amount of fuel in the engine oil will vaporize, and therefore the fuel content in the blowby gas will increase. As a result, blowby gas which contains a large amount of fuel will pass through the blowby gas passage and flow into the intake passage. For this reason, during fuel cut control, the large amount of fuel is mixed in the air taken into a cylinder. Due to this fuel, the oxygen in the exhaust gas is consumed in the exhaust passage, in particular the exhaust purification catalyst. As a result, the exhaust air-fuel ratio decreases during fuel cut control.

In the abnormality diagnosis system described in PTL 2, the fluctuation of the exhaust air-fuel ratio during fuel cut control is not considered at all. For this reason, in this abnormality diagnosis system, if the blowby gas causes the exhaust air-fuel ratio to decrease during fuel cut control, it is not possible to accurately diagnose abnormality of an air-fuel ratio sensor. Specifically, even if the air-fuel ratio sensor is normal, if blowby gas causes the exhaust air-fuel ratio to decrease during fuel cut control, the output current of the air-fuel ratio sensor and in turn the applied voltage will decrease, and therefore the normal air-fuel ratio sensor is liable to be mistakenly diagnosed as abnormal. Alternatively, if an increase in the output current and in turn the applied voltage due to an abnormality of an air-fuel ratio sensor is cancelled out by a decrease in the output current and in turn applied voltage due to a decrease in the exhaust air-fuel ratio during fuel cut control, the abnormal air-fuel ratio sensor will be mis-diagnosed as normal.

Therefore, in view of the above issues, an object of the present invention is to provide an abnormality diagnosis system of an air-fuel ratio sensor which enables an abnormality of an air-fuel ratio sensor to be precisely diagnosed even if blowby gas causes the exhaust air-fuel ratio to decrease during fuel cut control.

Solution to Problem

In order to solve the above problem, in a first invention, there is provided an abnormality diagnosis system of an air-fuel ratio sensor provided in an internal combustion engine, wherein the internal combustion engine has an intake passage in which a throttle valve is arranged and which leads an air-fuel mixture containing air and fuel to a combustion chamber, an exhaust passage discharging exhaust gas produced by combustion of the air-fuel mixture in the combustion chamber, and a blowby gas passage returning blowby gas in a crankcase to the downstream side of the throttle valve in the intake passage, the air-fuel ratio sensor is provided in the exhaust passage and detects an air-fuel ratio of the exhaust gas flowing through the exhaust passage, and the abnormality diagnosis system is configured to acquire a blowby gas flow ratio showing a ratio of the flow of blowby gas to the flow of gas to the combustion chamber and an output current of the air-fuel ratio sensor during fuel cut control in which the internal combustion engine stops the feed of fuel to the combustion chamber and at a plurality of points of time of different flows of blowby gas passing through the blowby gas passage and flowing to the downstream side of the throttle valve in the intake passage, calculate an output current of the air-fuel ratio sensor corresponding to a blowby gas flow ratio smaller than the blowby gas flow ratios acquired at the plurality of points of time, based on the blowby gas flow ratio and output current, and judge the air-fuel ratio sensor for abnormality based on the calculated output current.

In a second invention, the plurality of points of time are a plurality of points of time at a single cycle of fuel cut control in a first invention.

In a third invention, the blowby gas flow ratio smaller than the blowby gas flow ratios acquired at the plurality of points of time is zero in the first or second invention.

In a forth invention, the abnormality diagnosis system is configured to calculate an output gain of the air-fuel ratio sensor based on the calculated output current, calculate a rate of change of the calculated output gain to a reference value, and judge that the air-fuel ratio sensor is abnormal when the rate of change is outside a predetermined range in any one of the first to third inventions.

In a fifth invention, the abnormality diagnosis system is configured to calculate an amount of change of the blowby gas flow ratios acquired at the plurality of points of time, and not to judge abnormality of the air-fuel ratio when the amount of change is less than a predetermined value in any one of the first to fourth inventions.

In a sixth invention, the abnormality diagnosis system is configured to acquire values of a variation factor causing the output current of the air-fuel ratio sensor to fluctuate, other than the air-fuel ratio of the exhaust gas, at the plurality of points of time, calculate an amount of change of the values of the variation factor, and not to judge abnormality of the air-fuel ratio when the amount of change is a predetermined value or more in any one of the first to fifth inventions.

Advantageous Effects of Invention

According to the present invention, it is possible to provide a system for detecting abnormality able to differentiate a type of abnormality occurring at an air-fuel ratio sensor.

BRIEF DESCRIPTION OF DRAWINGS

FIGS. 7A to 7C are graphs which show the relationship between a blowby gas flow ratio and output current of an air-fuel ratio sensor during fuel cut control.

FIG. 22 is a flow chart which shows a control routine for processing for updating maximum values and minimum values of output current variation factors.

DESCRIPTION OF EMBODIMENTS

Figure 1:
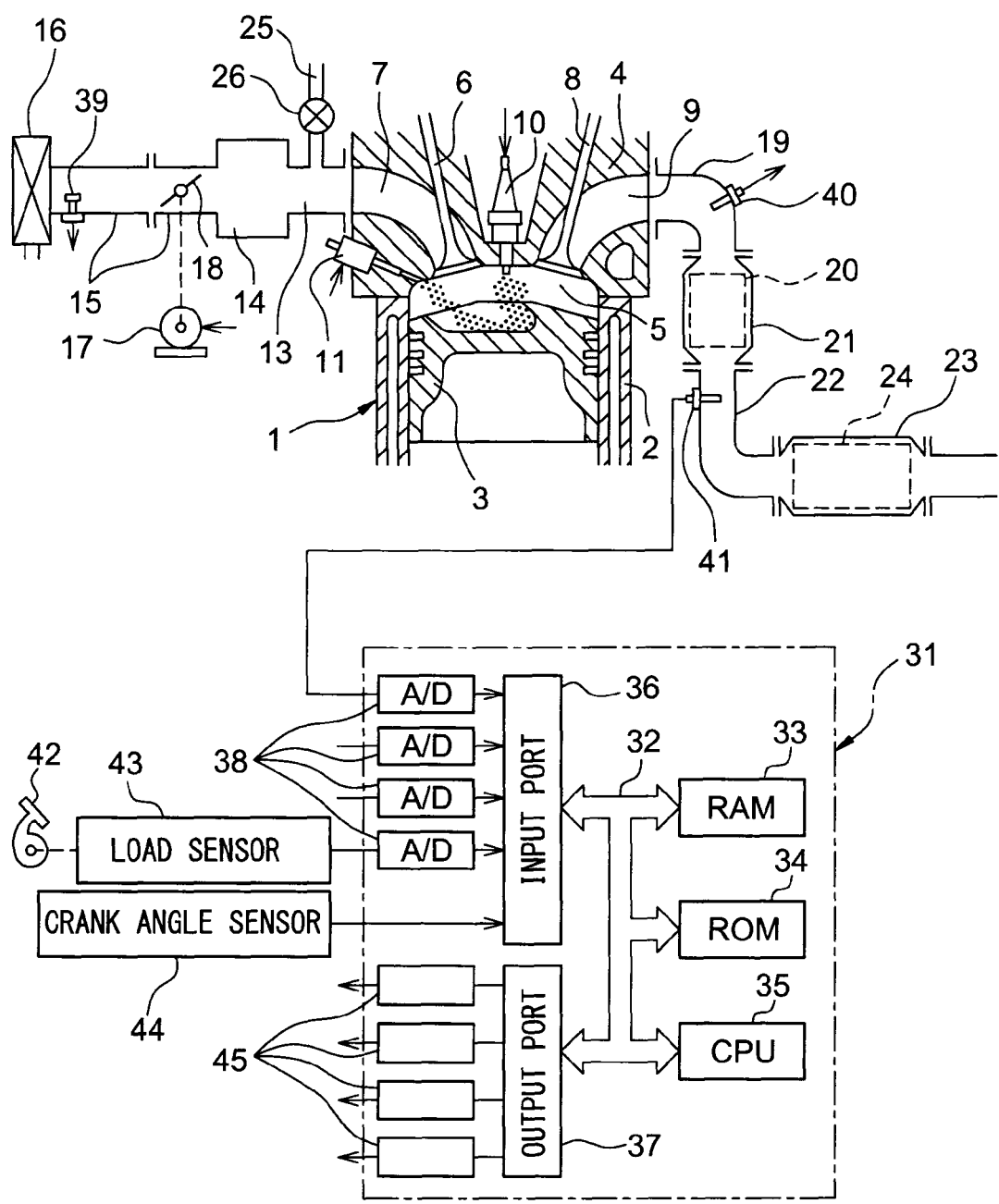
FIG. 1 is a view which schematically shows an internal combustion engine which uses an abnormality diagnosis system of an air-fuel ratio sensor according to an embodiment of the present invention.

Referring to the drawings, an embodiment of the present invention will be explained in detail below. Note that, in the following explanation, similar component elements are assigned the same reference numerals.

<Explanation of Internal Combustion Engine as a Whole>

FIG. 1 is a view which schematically shows an internal combustion engine in which an abnormality diagnosis system of an air-fuel ratio sensor according to an embodiment of the present invention is used. Referring to FIG. 1, 1 indicates an engine body, 2 a cylinder block, 3 a piston which reciprocates inside the cylinder block 2, 4 a cylinder head which is fastened to the cylinder block 2, 5 a combustion chamber which is formed between the piston 3 and the cylinder head 4, 6 an intake valve, 7 an intake port, 8 an exhaust valve, and 9 an exhaust port. The intake valve 6 opens and closes the intake port 7, while the exhaust valve 8 opens and closes the exhaust port 9.

As shown in FIG. 1, at the center part of the inside wall surface of the cylinder head 4, a spark plug 10 is arranged. A fuel injector 11 is arranged around the inside wall surface of the cylinder head 4. The spark plug 10 is configured to cause generation of a spark in accordance with an ignition signal. Further, the fuel injector 11 directly injects a predetermined amount of fuel into the combustion chamber 5 in accordance with an injection signal. That is, the internal combustion engine of the present embodiment is a cylinder injection type internal combustion engine. Note that, the internal combustion engine may also be a port injection type internal combustion engine. In this case, the fuel injector 11 is arranged so as to inject fuel inside the intake port 7. Further, in the present embodiment, as the fuel, gasoline with a stoichiometric air-fuel ratio of 14.6 is used. However, in the internal combustion engine in which the abnormality diagnosis system of an air-fuel ratio sensor of the present invention is used, another fuel may also be used.

The intake port 7 in each cylinder is connected through a corresponding intake runner 13 to a surge tank 14. The surge tank 14 is connected through an intake pipe 15 to an air cleaner 16. The intake port 7, intake runner 13, surge tank 14, and intake pipe 15 form an intake passage which leads an air-fuel mixture which contains air and fuel to a combustion chamber 5. Further, inside the intake pipe 15, a throttle valve 18 which is driven by a throttle valve drive actuator 17 is arranged. The throttle valve 18 can be turned by the throttle valve drive actuator 17 to thereby change the opening area of the intake passage.

On the other hand, the exhaust port 9 in each cylinder is connected to an exhaust manifold 19. The exhaust manifold 19 has a plurality of runners which are connected to the exhaust ports 9 and a header at which these runners are collected. The header of the exhaust manifold 19 is connected to an upstream side casing 21 which has an upstream side exhaust purification catalyst 20 built into it. The upstream side casing 21 is connected through an exhaust pipe 22 to a downstream side casing 23 which has a downstream side exhaust purification catalyst 24 built into it. The exhaust port 9, exhaust manifold 19, upstream side casing 21, exhaust pipe 22, and downstream side casing 23 form an exhaust passage which discharges exhaust gas produced due to combustion of the air-fuel mixture in the combustion chamber 5.

Further, an intake runner 13 is connected through a blowby gas passage 25 to the crankcase. Inside the blowby gas passage 25, a PCV (positive crankcase ventilation) valve 26 is arranged. The PCV valve 26 is a one-way valve (check valve) which allows flow only in one direction from the crankcase to the intake runner 13. If a negative pressure occurs at the intake runner 13, the PCV valve 26 opens and air-fuel mixture leaks from the clearance between the piston 3 and the cylinder block 2 to the inside of the crankcase and so-called blowby gas runs from the inside of the crankcase through the inside of the blowby gas passage 25 to be returned to the intake runner 13. Note that, the blowby gas passage 25 may be connected to another position in the intake passage at the downstream side of the throttle valve 18, for example, the surge tank 14.

The electronic control unit (ECU) 31 is comprised of a digital computer which is provided with components which are connected together through a bidirectional bus 32 such as a RAM (random access memory) 33, ROM (read only memory) 34, CPU (microprocessor) 35, input port 36, and output port 37. In the intake pipe 15, an air flow meter 39 is arranged for detecting the flow rate of air which flows through the intake pipe 15. The output of this air flow meter 39 is input through a corresponding AD converter 38 to the input port 36. Further, at the header of the exhaust manifold 19, an upstream side air-fuel ratio sensor 40 is arranged which detects the air-fuel ratio of the exhaust gas which flows through the inside of the exhaust manifold 19 (that is, the exhaust gas which flows into the upstream side exhaust purification catalyst 20). In addition, in the exhaust pipe 22, a downstream side air-fuel ratio sensor 41 is arranged which detects the air-fuel ratio of the exhaust gas flowing through the inside of the exhaust pipe 22 (that is, the exhaust gas which flows out from the upstream side exhaust purification catalyst 20 and flows into the downstream side exhaust purification catalyst 24). The outputs of these air-fuel ratio sensors 40 and 41 are also input through the corresponding AD converters 38 to the input port 36. Note that, the configurations of these air-fuel ratio sensors 40 and 41 will be explained later.

Further, an accelerator pedal 42 has a load sensor 43 connected to it which generates an output voltage which is proportional to the amount of depression of the accelerator pedal 42. The output voltage of the load sensor 43 is input to the input port 36 through a corresponding AD converter 38. The crank angle sensor 44 generates an output pulse every time, for example, a crankshaft rotates by 15 degrees. This output pulse is input to the input port 36. The CPU 35 calculates the engine speed from the output pulse of this crank angle sensor 44. On the other hand, the output port 37 is connected through corresponding drive circuits 45 to the spark plugs 10, fuel injectors 11, and throttle valve drive actuator 17. Note that, ECU 31 acts as a control system for controlling the internal combustion engine.

The upstream side exhaust purification catalyst 20 and the downstream side exhaust purification catalyst 24 are three-way catalysts which have oxygen storage abilities. Specifically, the exhaust purification catalysts 20 and 24 are comprised of carriers comprised of ceramic on which a precious metal having a catalytic action (for example, platinum (Pt)) and a substance having an oxygen storage ability (for example, ceria ($CeO_2$)) are carried. The exhaust purification catalysts 20 and 24 exhibit a catalytic action of simultaneously removing unburned gas (HC, CO, etc.) and nitrogen oxides ($NO_x$) when reaching a predetermined activation temperature and, in addition, an oxygen storage ability.

According to the oxygen storage ability of the exhaust purification catalysts 20 and 24, the exhaust purification catalysts 20 and 24 store the oxygen in the exhaust gas when the air-fuel ratio of the exhaust gas flowing into the exhaust purification catalysts 20 and 24 is an air-fuel ratio leaner than the stoichiometric air-fuel ratio (hereinafter, also referred to as "lean air-fuel ratio"). On the other hand, the exhaust purification catalysts 20 and 24 release the oxygen stored in the exhaust purification catalysts 20 and 24 when the inflowing exhaust gas has an air-fuel ratio richer than the stoichiometric air-fuel ratio (hereinafter, also referred to as "rich air-fuel ratio"). As a result, as long as the oxygen storage ability of the exhaust purification catalysts 20 and 24 is maintained, the air-fuel ratio of the exhaust gas flowing out from the exhaust purification catalysts 20 and 24 becomes substantially stoichiometric air-fuel ratio, regardless the air-fuel ratio of the exhaust gas flowing into the exhaust purification catalyst 20 and 24.

<Explanation of Air-Fuel Ratio Sensor>

Figure 2:
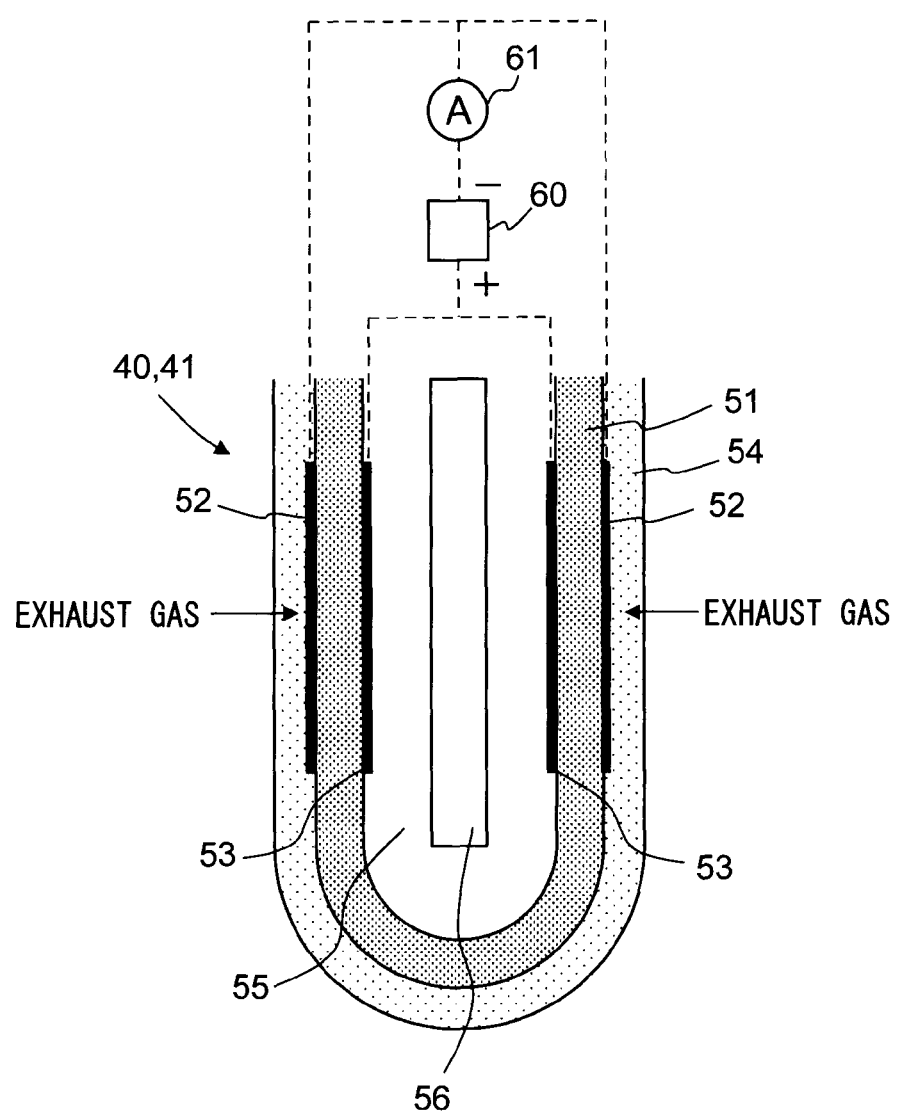
FIG. 2 is a view which schematically shows the structure of an air-fuel ratio sensor.

In the present embodiment, as the air-fuel ratio sensors 40 and 41, cup type limit current type air-fuel ratio sensors are used. Referring to FIG. 2, the structures of the air-fuel ratio sensors 40 and 41 are simply explained. FIG. 2 is a view which schematically shows the structure of an air-fuel ratio sensor. Each of the air-fuel ratio sensors 40 and 41 is provided with a solid electrolyte layer 51, an exhaust side electrode 52 arranged on one side surface of the solid electrolyte layer 51, an atmosphere side electrode 53 arranged on the other side surface of the solid electrolyte layer 51, a diffusion regulation layer 54 regulating the diffusion of the flowing exhaust gas, a reference gas chamber 55, and a heater part 56 heating the air-fuel ratio sensor 40 or 41, in particular the electrolyte layer (element) 51.

In each of the cup type air-fuel ratio sensors 40 and 41 of the present embodiment, the solid electrolyte layer 51 is formed into a cylindrical shape with one closed end. Inside of the reference gas chamber 55 defined inside of the air-fuel ratio sensor 40 or 41, atmospheric gas (air) is introduced and the heater part 56 is arranged. On the inside surface of the solid electrolyte layer 51, an atmosphere side electrode 53 is arranged. On the outside surface of the solid electrolyte layer 51, an exhaust side electrode 52 is arranged. On the outside surfaces of the solid electrolyte layer 51 and the exhaust side electrode 52, a diffusion regulation layer 54 is arranged to cover the solid electrolyte layer 51 and the exhaust side electrode 52. Note that, at the outside of the diffusion regulation layer 54, a protective layer (not shown) may be provided for preventing a liquid etc. from depositing on the surface of the diffusion regulation layer 54.

The solid electrolyte layer 51 is formed by a sintered body of $ZrO_2$ (zirconia), $HfO_2$, $ThO_2$, $Bi_2O_3$, or other oxygen ion conducting oxide in which CaO, MgO, $Y_2O_3$, $Yb_2O_3$, etc. is blended as a stabilizer. Further, the diffusion regulation layer 54 is formed by a porous sintered body of alumina, magnesia, silica, spinel, mullite, or another heat resistant inorganic substance. Furthermore, the exhaust side electrode 52 and atmosphere side electrode 53 is formed by platinum or other precious metal with a high catalytic activity.

Further, between the exhaust side electrode 52 and the atmosphere side electrode 53, sensor applied voltage V is supplied by the voltage control device 60 mounted on the ECU 31. In addition, the ECU 31 is provided with a current detection device 61 which detects the current flowing between these electrodes 52 and 53 through the solid electrolyte layer 51 when the sensor applied voltage is supplied.

The current which is detected by this current detection device 61 is the output current of the air-fuel ratio sensors 40 and 41.

Figure 3:
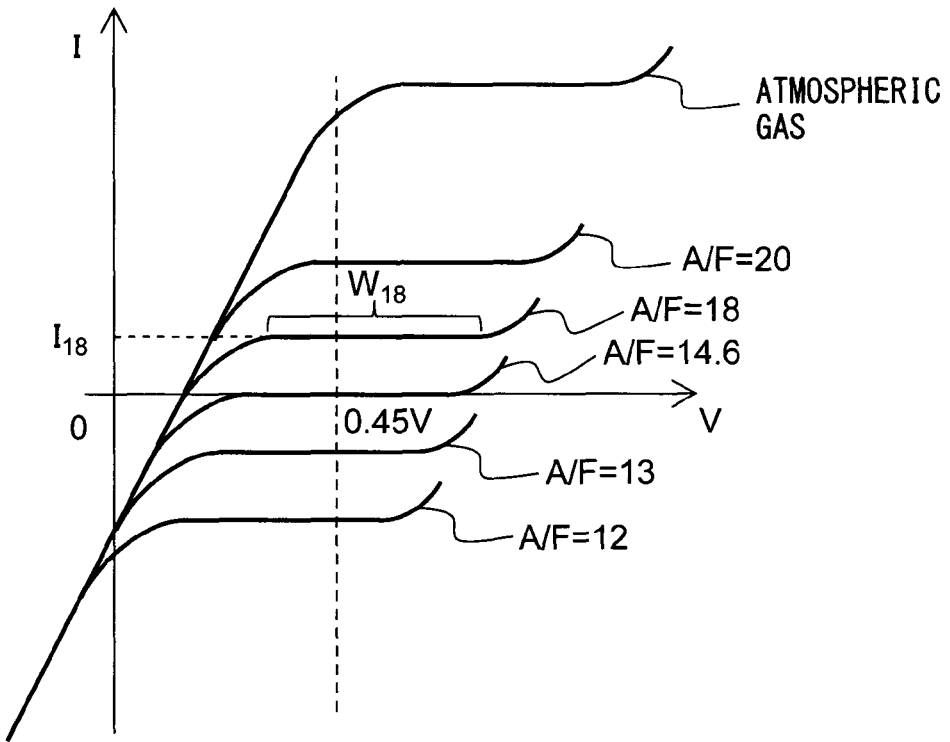
FIG. 3 is a view which shows the relationship between a sensor applied voltage and output current at different exhaust air-fuel ratios.

The thus configured air-fuel ratio sensors 40 and 41 have the voltage-current (V-I) characteristic such as shown in FIG. 3. FIG. 3 is a view which shows the relationship between sensor applied voltage and output current at different exhaust air-fuel ratios. As will be understood from FIG. 3, the output current I becomes larger the higher the exhaust air-fuel ratio (the leaner). Further, at the line V-I of each exhaust air-fuel ratio, there is a region parallel to the V axis, that is, a region where the output current does not change much at all even if the sensor applied voltage changes. This voltage region is called the "limit current region". The current at this time is called the "limit current". In FIG. 3, the limit current region and limit current when the exhaust air-fuel ratio is 18 are shown by $W_{18}$ and $1_{18}$.

On the other hand, in the region where the sensor applied voltage is lower than the limit current region, the output current changes substantially proportionally to the sensor applied voltage. Below, this region will be referred to as the "proportional region". The slope at this time is determined by the DC element resistance of the solid electrolyte layer 51. Further, in the region where the sensor applied voltage is higher than the limit current region, the output current also increases along with the increase in the sensor applied voltage. In this region, breakdown of the moisture, which is contained in the exhaust gas, on the exhaust side electrode 52, etc. causes the output current to change according to change of the sensor applied voltage. This region will be referred to as the "moisture breakdown region" below.

Figure 4:
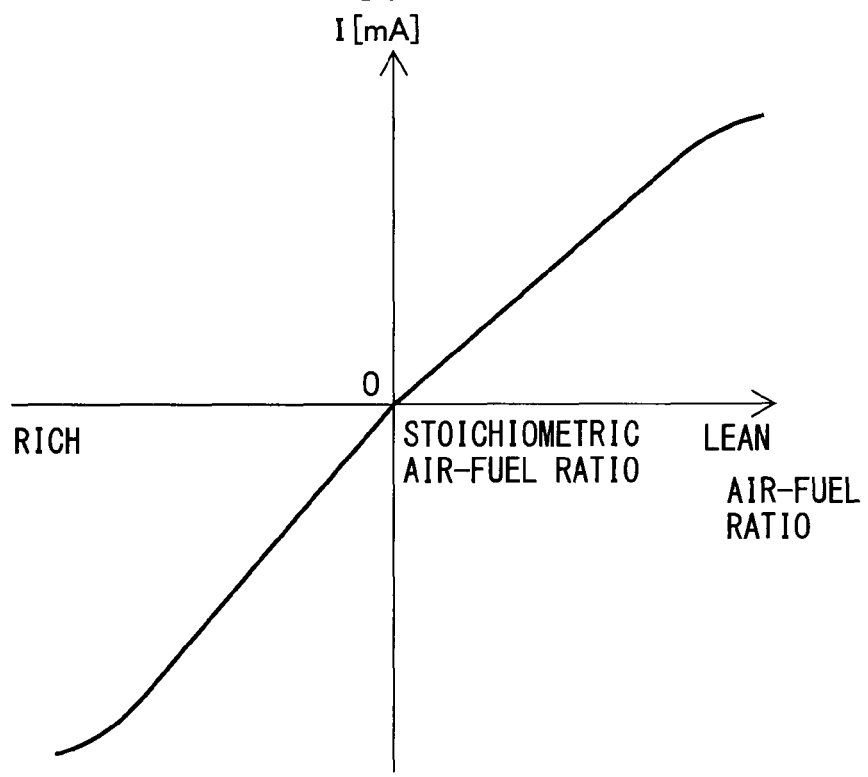
FIG. 4 is a view which shows the relationship between an exhaust air-fuel ratio and output current when making the sensor applied voltage constant.

FIG. 4 is a view which shows the relationship between the exhaust air-fuel ratio and the output current I when making the supplied voltage constant at about 0.45V. As will be understood from FIG. 4, in the air-fuel ratio sensors 40 and 41, the output current I changes linearly (proportionally) with respect to the exhaust air-fuel ratio so that the higher the exhaust air-fuel ratio (that is, the leaner), the greater the output current I from the air-fuel ratio sensors 40 and 41. In addition, the air-fuel ratio sensors 40 and 41 are configured so that the output current I becomes zero when the exhaust air-fuel ratio is the stoichiometric air-fuel ratio. Further, when the exhaust air-fuel ratio becomes larger by a certain extent or more or when it becomes smaller by a certain extent or more, the ratio of change of the output current to the change of the exhaust air-fuel ratio becomes smaller.

Note that, in the above example, as the air-fuel ratio sensors 40 and 41, limit current type air-fuel ratio sensors of the structure shown in FIG. 2 are used. However, any type of air-fuel ratio sensor can be used as the air-fuel ratio sensors 40 and 41, as long as the output current linearly changes with respect to the exhaust air-fuel ratio. Therefore, as the air-fuel ratio sensors 40 and 41, for example, it is also possible to use a layered-type limit current type air-fuel ratio sensor or other structure of limit current type air-fuel ratio sensor or air-fuel ratio sensor not a limit current type or any other air-fuel ratio sensor. Further, the air-fuel ratio sensors 40 and 41 may be air-fuel ratio sensors having different construction from each other.

<Basic Air-Fuel Ratio Control>

In the thus configured internal combustion engine, based on the outputs of the air-fuel ratio sensors 40 and 41, the amount of fuel injection from the fuel injector 11 is set so that the air-fuel ratio of the exhaust gas flowing into the upstream side exhaust purification catalyst 20 becomes the optimum air-fuel ratio based on the engine operating state. In the present embodiment, based on the output current of the upstream side air-fuel ratio sensor 40 (corresponding to air-fuel ratio of exhaust gas flowing into the upstream side exhaust purification catalyst 20 or air-fuel ratio of exhaust gas flowing out from the engine body), feedback control is carried out so that this output current becomes a value corresponding to the target air-fuel ratio. In addition, the target air-fuel ratio is changed based on the output current of the downstream side air-fuel ratio sensor 41.

Figure 5:
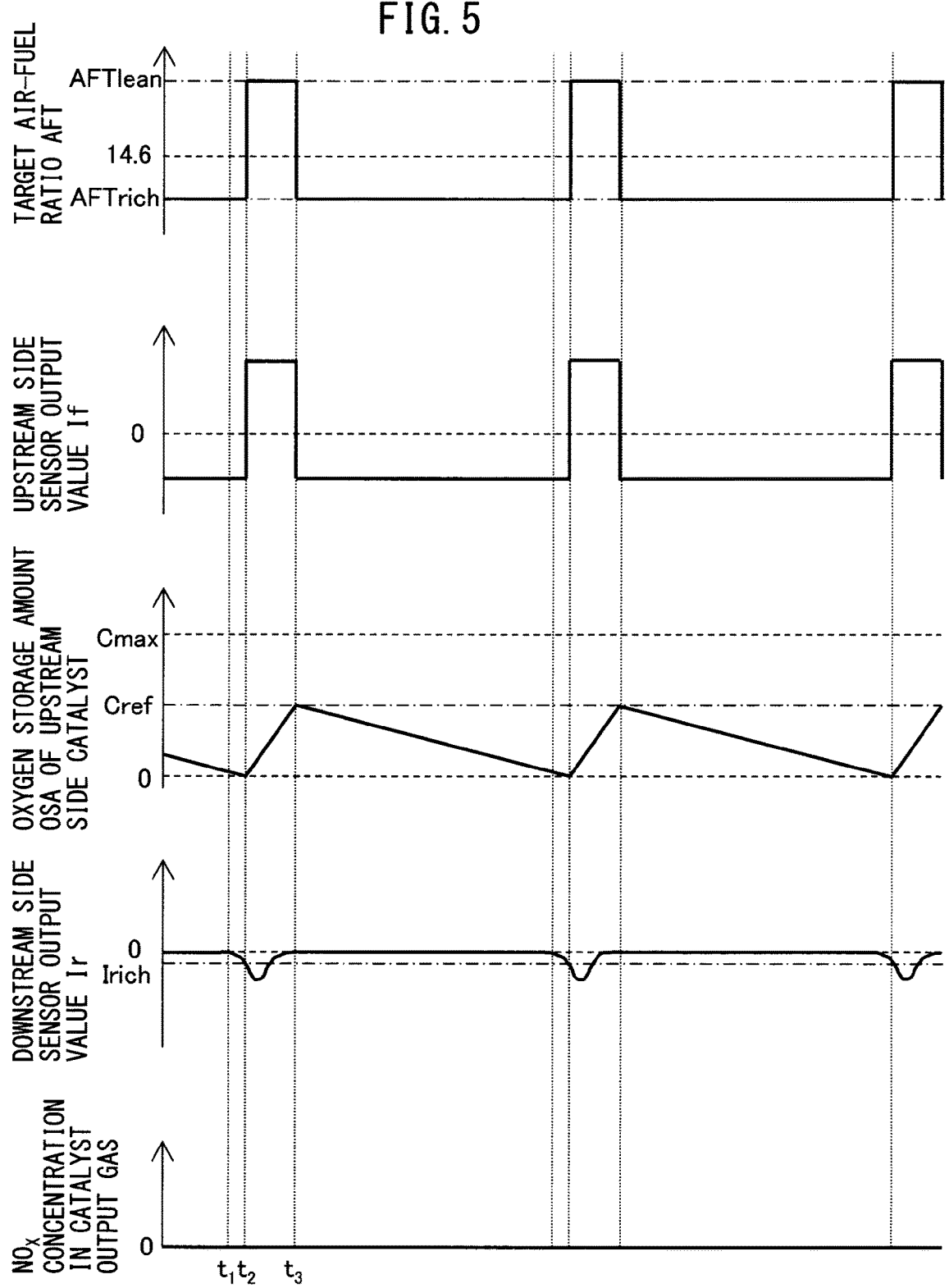
FIG. 5 is a time chart of a target air-fuel ratio etc. at the time of normal operation of an internal combustion engine.

Referring to FIG. 5, such an example of control of the target air-fuel ratio will be simply explained. FIG. 5 is a time chart of the target air-fuel ratio AFT, the output current (output value) If of the upstream side air-fuel ratio sensor 40, the oxygen storage amount OSA of the upstream side exhaust purification catalyst, and the output current (output value) Ir of the downstream side air-fuel ratio sensor 41, at the time of ordinary operation of the internal combustion engine.

Note that, the output currents of the air-fuel ratio sensors 40, 41, as shown in FIG. 4, become zero when the air-fuel ratio of the exhaust gas flowing around the air-fuel ratio sensors 40, 41 is the stoichiometric air-fuel ratio. In addition, they become negative values when the air-fuel ratio of the exhaust gas is the rich air-fuel ratio, and become positive values when the air-fuel ratio of the exhaust gas is the lean air-fuel ratio. Further, when the air-fuel ratio of the exhaust gas flowing around the air-fuel ratio sensors 40, 41 is the rich air-fuel ratio or lean air-fuel ratio, the larger the difference from the stoichiometric air-fuel ratio becomes, the larger the absolute values of the output currents of the air-fuel ratio sensors 40, 41 become. Further, the "time of normal operation (normal control)" means an operating state (control state) where control for adjusting the amount of fuel injection in accordance with a specific operating state of the internal combustion engine (for example, correction for increasing amount of fuel injection performed at time of acceleration of vehicle mounting an internal combustion engine or fuel cut control which will be explained later, etc.) is not being performed.

In the example shown in FIG. 5, when the output current Ir of the downstream side air-fuel ratio sensor 41 becomes equal to or less than a rich judgment reference value Irich smaller than zero, the target air-fuel ratio is set to and maintained at a lean set air-fuel ratio AFTlean (for example, 15) which is leaner than the stoichiometric air-fuel ratio. In this regard, the rich judgment reference value Irich is a value which corresponds to a predetermined rich judgment air-fuel ratio (for example, 14.55) which is slightly richer than the stoichiometric air-fuel ratio.

Then, the oxygen storage amount of the upstream side exhaust purification catalyst 20 is estimated. If this estimated value is equal to or greater than a predetermined judgment reference storage amount Cref (amount smaller than maximum storable oxygen amount Cmax), the target air-fuel ratio is set to and maintained at a rich set air-fuel ratio AFTrich (for example, 14.4) which is richer than the stoichiometric air-fuel ratio. In the example shown in FIG. 5, this operation is repeatedly performed.

Specifically, in the example shown in FIG. 5, before the time $t_1$, the target air-fuel ratio AFT is set to the rich set air-fuel ratio AFTrich and, accordingly, the output current If of the upstream side air-fuel ratio sensor 40 is a value smaller than zero (corresponding to rich air-fuel ratio). Further, the upstream side exhaust purification catalyst 20 stores oxygen, and therefore the output current Ir of the downstream side air-fuel ratio sensor 41 becomes substantially zero (corresponding to stoichiometric air-fuel ratio). At this time, the air-fuel ratio of the exhaust gas flowing into the upstream side exhaust purification catalyst 20 becomes a rich air-fuel ratio, and therefore the upstream side exhaust purification catalyst 20 gradually falls in oxygen storage amount.

Then, at the time $t_1$, the oxygen storage amount of the upstream side exhaust purification catalyst 20 approaches zero, whereby part of the unburned gas flowing into the upstream side exhaust purification catalyst 20 starts to flow out without being purified at the upstream side exhaust purification catalyst 20. As a result, at the time $t_2$, the output current Ir of the downstream side air-fuel ratio sensor 41 becomes equal to or less than the rich judgment reference value Irich (corresponding to rich judgment reference air-fuel ratio). At this time, the target air-fuel ratio is switched from the rich set air-fuel ratio AFTrich to the lean set air-fuel ratio AFTlean.

By switching the target air-fuel ratio, the air-fuel ratio of the exhaust gas flowing into the upstream side exhaust purification catalyst 20 becomes a lean air-fuel ratio, and the outflow of unburned gas decreases and stops. Further, the oxygen storage amount OSA of the upstream side exhaust purification catalyst 20 gradually increases and, at the time $t_3$, reaches the judgment reference storage amount Cref. If, in this way, the oxygen storage amount reaches the judgment reference storage amount Cref, the target air-fuel ratio again is switched from the lean set air-fuel ratio AFTlean to the rich set air-fuel ratio AFTrich. By this switching of the target air-fuel ratio, the air-fuel ratio of the exhaust gas flowing into the upstream side exhaust purification catalyst 20 again becomes a rich air-fuel ratio. As a result, the oxygen storage amount of the upstream side exhaust purification catalyst 20 gradually decreases. Then, such operation is repeatedly performed. By performing such control, outflow of $NO_x$ from the upstream side exhaust purification catalyst 20 can be prevented.

Note that, the control of the air-fuel ratio performed at the time of normal operation is not necessarily limited to control such as explained above, based on the outputs of the upstream side air-fuel ratio sensor 40 and downstream side air-fuel ratio sensor 41. So long as control based on the outputs of these air-fuel ratio sensors 40, 41, it may be any control.

<Fuel Cut Control>

Further, in the internal combustion engine of the present embodiment, at the time of deceleration of the vehicle mounting the internal combustion engine, etc., fuel cut control is performed for stopping the injection of fuel from the fuel injector 11 to stop the feed of fuel into the combustion chamber 5 during operation of the internal combustion engine. This fuel cut control is started when a predetermined condition for start of fuel cut stands. Specifically, fuel cut control is, for example, performed when the amount of depression of the accelerator pedal 42 is zero or substantially zero (that is, engine load is zero or substantially zero) and the engine speed is equal to or greater than a predetermined speed higher than the speed at the time of idling.

When fuel cut control is performed, air or exhaust gas similar to air is exhausted from the internal combustion engine, and therefore gas with an extremely high air-fuel ratio (that is, extremely high lean degree) flows into the upstream side exhaust purification catalyst 20. As a result, during fuel cut control, a large amount of oxygen flows into the upstream side exhaust purification catalyst 20, and the oxygen storage amount of the upstream side exhaust purification catalyst 20 reaches the maximum storable oxygen amount.

Further, the fuel cut control is made to end if a predetermined condition for ending the fuel cut stands. As the condition for ending the fuel cut, for example, the amount of depression of the accelerator pedal 42 becoming a predetermined value or more (that is, the engine load becoming a certain extent of value) or the engine speed becoming equal to or less than a predetermined speed higher than the speed at the time of idling, etc. may be mentioned. Further, in the internal combustion engine of the present embodiment, right after the end of the fuel cut control, post-return rich control is performed which makes the air-fuel ratio of the exhaust gas flowing into the upstream side exhaust purification catalyst 20 a post-return rich air-fuel ratio which is richer than the rich set air-fuel ratio. Due to this, it is possible to quickly release the oxygen stored in the upstream side exhaust purification catalyst 20 during fuel cut control.

<Diagnosis of Abnormality of Air-Fuel Ratio Sensor>

In this regard, as explained above, the air-fuel ratio sensors 40, 41 deteriorate along with their use, and thus sometimes the air-fuel ratio sensors 40, 41 become abnormal. If the air-fuel ratio sensors 40, 41 become abnormal in this way, the precision of output deteriorates, and thus the amount of fuel injection from the fuel injector 11 can no longer be suitably controlled. As a result, deterioration of the exhaust emission or deterioration of the fuel economy is invited. Therefore, the internal combustion engine of the present embodiment is provided with an abnormality diagnosis system which self-diagnoses abnormality of the air-fuel ratio sensors 40, 41.

As abnormality diagnosis control performed by such an abnormality diagnosis system, for example, the one which is performed at the time of fuel cut control may be mentioned. If fuel cut control wherein the feed of fuel to a combustion chamber 5 is stopped is performed, usually exhaust gas which does not contain much fuel at all is exhausted from the combustion chamber 5. For this reason, the concentration of oxygen in the exhaust gas which flows into the air-fuel ratio sensors 40 and 41 becomes substantially equal to the concentration of oxygen in the atmosphere (about 20%). In this case, the output currents of the air-fuel ratio sensors 40 and 41 become maximum. The values are known in advance. Therefore, by judging if the output current actually detected at the time of fuel cut control is within predetermined reference range, it is possible to diagnose abnormality of the air-fuel ratio sensor 40 or 41.

<Problem Points in Abnormality Diagnosis>

However, if fuel cut control is performed, usually a negative pressure is generated at the downstream side of the throttle valve 18 in the intake passage, and therefore the blowby gas is returned to the downstream side of the throttle valve 18 in the intake passage. The fuel in the blowby gas causes the oxygen in the exhaust gas to be consumed in the exhaust passage, in particular, the upstream side exhaust purification catalyst 20, and therefore the concentration of oxygen in the exhaust gas which reaches the air-fuel ratio sensors 40 and 41 falls. As a result, the output currents of the air-fuel ratio sensors 40 and 41 also fall, and therefore the abnormality diagnosis system is liable to misdiagnose normal air-fuel ratio sensors 40 or 41 as being abnormal. Alternatively, if an increase in output current of the air-fuel ratio sensor 40 or 41 due to abnormality is cancelled out by a decrease in output current due to the drop in concentration of oxygen in the exhaust gas during fuel cut control, the abnormality diagnosis system will misdiagnosis the abnormal air-fuel ratio sensor 40 or 41 as being normal.

<Abnormality Diagnosis in Present Invention>

Therefore, in order to raise the precision of abnormality diagnosis of the air-fuel ratio sensor 40 or 41, the abnormality diagnosis system of the air-fuel ratio sensor 40 or 41 according to an embodiment of the present invention diagnoses abnormality by acquiring a blowby gas flow ratio showing a ratio of the flow of blowby gas to the flow of gas to the combustion chamber 5 and an output current of the air-fuel ratio sensor 40 or 41 during fuel cut control at a plurality of points of time of different flows of blowby gas which pass through the blowby gas passage 25 and flow to the downstream side of the throttle valve 18 in the intake passage and by calculating an output current of the air-fuel ratio sensor 40 or 41 corresponding to a blowby gas flow ratio smaller than the blowby gas flow ratios acquired at the plurality of points of time, based on the acquired blowby gas flow ratios and output currents.

<Principle of Present Invention>

Figure 6:
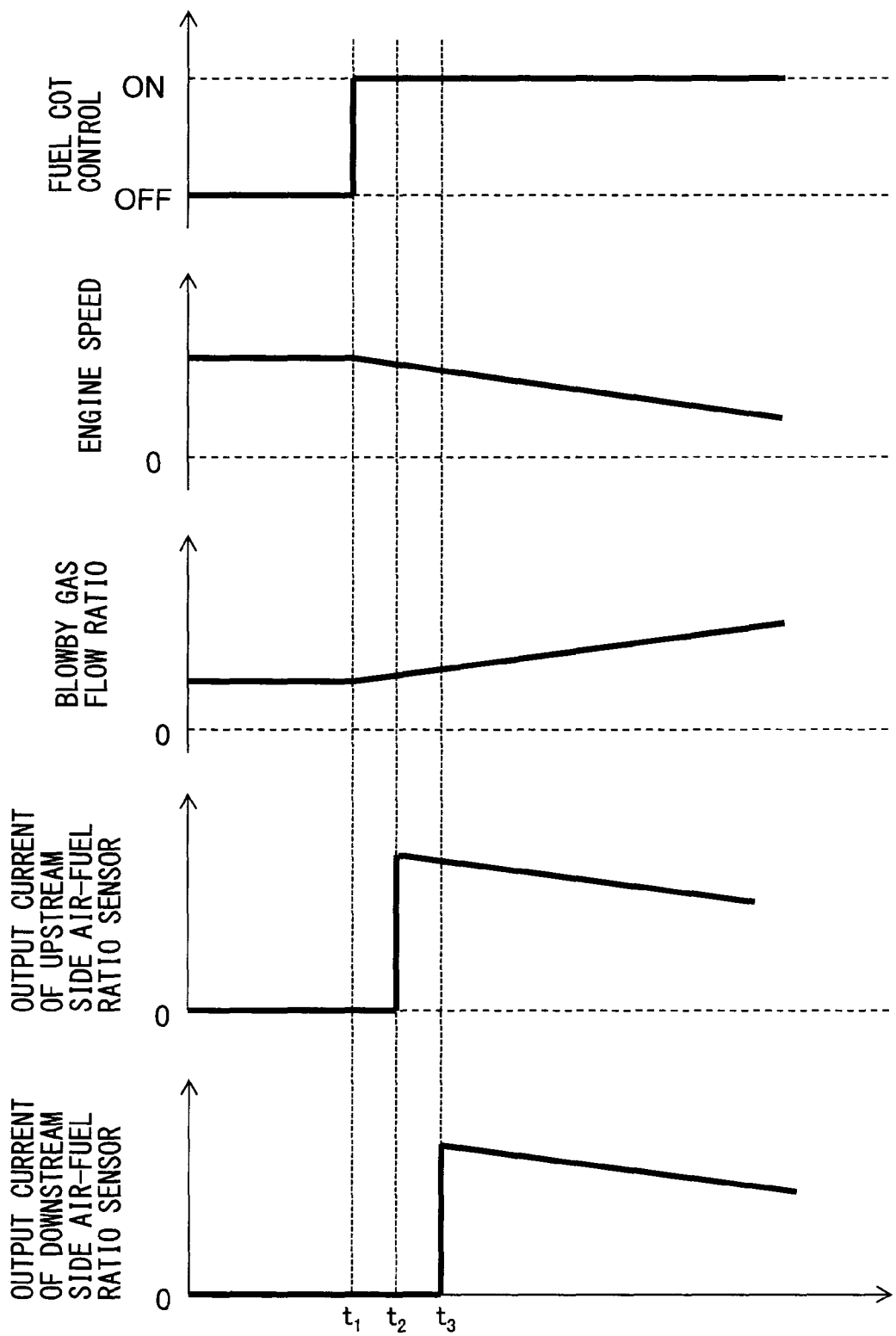
FIG. 6 is a schematic time chart of engine speed etc. before and after fuel cut control of an internal combustion engine.

First, referring to FIG. 6, one example of the changes in the engine speed, blowby gas flow ratio, output current of the upstream side air-fuel ratio sensor 40, and output current of the downstream side air-fuel ratio sensor 41 before and after fuel cut control will be explained. FIG. 6 is a schematic time chart of the engine speed, blowby gas flow ratio, output current of the upstream side air-fuel ratio sensor 40, and output current of the downstream side air-fuel ratio sensor 41 before and after fuel cut control of the internal combustion engine.

In the example which is shown in FIG. 6, before fuel cut control, the target air-fuel ratio is made the stoichiometric air-fuel ratio, and the output current of the upstream side air-fuel ratio sensor 40 and the output current of the downstream side air-fuel ratio sensor 41 are zero. Further, the engine speed and blowby gas flow ratio before fuel cut control are constant.

In the example shown in FIG. 6, at the time $t_1$, fuel cut control is started. After the start of fuel cut control, the engine speed usually decrease along with time, except when driving on a descending slope etc. If the engine speed decreases, usually the pressure in the intake passage at the downstream side of the throttle valve 18 decreases (becomes negative pressure), and therefore the flow of blowby gas flowing into the intake passage and in turn the blowby gas flow ratio increases.

At the time $t_2$ after start of fuel cut control, if the air fed into the combustion chamber 5 along with fuel cut control reaches the upstream side air-fuel ratio sensor 40, the output current of the upstream side air-fuel ratio sensor 40 becomes a value larger than zero. Further, after the time $t_2$, if air flows into the upstream side exhaust purification catalyst 20, the oxygen storage amount of the upstream side exhaust purification catalyst 20 reaches the maximum storable oxygen amount. For this reason, in the illustrated example, at the time $t_3$, the air reaches the downstream side air-fuel ratio sensor 41, and the output current of the downstream side air-fuel ratio sensor 41 becomes a value larger than zero.

If the increase in the blowby gas flow ratio causes an increase in the oxygen in the exhaust gas consumed by the fuel in the blowby gas, the exhaust air-fuel ratio and in turn the output currents of the air-fuel ratio sensors 40 and 41 will fall. In this example, after fuel cut control, the blowby gas flow ratio gradually increases, and therefore as shown in FIG. 6, the air reaches the air-fuel ratio sensors 40 and 41, then the output currents of the air-fuel ratio sensors 40 and 41 gradually fall.

Note that, in the example shown in FIG. 6, to facilitate understanding of the explanation, a simple model was explained, but the engine speed etc. do not necessarily change as shown in FIG. 6 before and after fuel cut control. For example, the pressure at the downstream side of the throttle valve 18 inside the intake passage is influenced by the intake temperature of the intake passage, the opening degree of the throttle valve 18, etc. in addition to the engine speed, and therefore in actuality, the blowby gas flow ratio can change different from the time chart shown in FIG. 6.

In the present invention, when diagnosing abnormality of the upstream side air-fuel ratio sensor 40, the blowby gas flow ratio and output current of the upstream side air-fuel ratio sensor 40 are acquired at a plurality of points of time from the time $t_2$ on. Further, when diagnosing abnormality of the downstream side air-fuel ratio sensor 41, the blowby gas flow ratio and the output current of the downstream side air-fuel ratio sensor 41 are acquired at a plurality of points of time from the time $t_3$ on.

As a result, graphs such as shown in FIGS. 7A to 7C are obtained in accordance with the amount of fuel which is contained in the flow of blowby gas. FIGS. 7A to 7C are graphs which show the relationship between the blowby gas flow ratio and the output current of the air-fuel ratio sensor 40 or 41 during fuel cut control. In FIGS. 7A to 7C, the values of the blowby gas flow ratio and the output current of the air-fuel ratio sensor 40 or 41 acquired at a plurality of points of time during fuel cut control are plotted on the graphs as diamond marks. Based on these values, as shown in FIGS. 7A to 7C, the relationship between the blowby gas flow ratio and the output current of the air-fuel ratio sensor 40 or 41 can be approximated by a first order line.

As explained above, if an increase in the blowby gas flow ratio causes an increase in the oxygen in the exhaust gas consumed by the fuel in the blowby gas, the exhaust air-fuel ratio and in turn the output currents of the air-fuel ratio sensors 40 and 41 fall. In this case, the slope of the first order approximation line, as shown in FIGS. 7B and 7C, becomes negative. The absolute value of the slope becomes larger the larger the amount of fuel contained in the blowby gas. FIG. 7B shows the relationship between the blowby gas flow ratio and the output current of the air-fuel ratio sensor 40 or 41 in the case where the fuel contained in the blowby gas is small in amount. FIG. 7C shows the relationship between the blowby gas flow ratio and the output current of the air-fuel ratio sensor 40 or 41 in the case where the fuel contained in the blowby gas is large in amount. On the other hand, if the blowby gas does not contain almost any fuel, as shown in FIG. 7A, the output current of the air-fuel ratio sensor 40 or 41 becomes a substantially constant value without regard as to the blowby gas flow ratio. Further, as will be understood from FIGS. 7A to 7C, the intercept "b" of the first order approximation line becomes substantially the same value regardless of the amount of fuel contained in the blowby gas.

As will be understood from FIGS. 7A to 7C, the intercept "b" of the first order approximation line corresponds to the output current of the air-fuel ratio sensor 40 or 41 when the blowby gas flow ratio is zero, that is, the output current of the air-fuel ratio sensor 40 or 41 corresponding to the concentration of oxygen in the air. The slope and intercept "b" of the first order approximation line can be calculated by the known least square method. For this reason, even if the blowby gas causes the exhaust air-fuel ratio during the fuel cut control to decrease, it is possible to estimate the output current of the air-fuel ratio sensor 40 or 41 corresponding to the concentration of oxygen in the air, based on the blowby gas flow ratios and the output currents of an air-fuel ratio sensor 40 or 41 acquired at a plurality of points of time, and in turn it is possible to precisely diagnose abnormality of the air-fuel ratio sensor 40 or 41.

Note that, instead of calculating the output current of the air-fuel ratio sensor 40 or 41 when the blowby gas flow ratio is zero, by calculating the output current the an air-fuel ratio sensor 40 or 41 corresponding to a blowby gas flow ratio smaller than the blowby gas flow ratios acquired at the plurality of points of time, it is possible to reduce the effect of the drop in output current due to the decrease in exhaust air-fuel ratio during fuel cut control due to blowby gas, and therefore it is possible to raise the precision of diagnosis of abnormality of the air-fuel ratio sensor 40 or 41.

A plurality of embodiments regarding an abnormality diagnosis system of the air-fuel ratio sensor 40 or 41 will be explained below.

First Embodiment

First, referring to FIG. 8 to FIG. 12, a first embodiment of the present invention will be explained. The abnormality diagnosis system of the first embodiment is configured to calculate the output current of the air-fuel ratio sensor 40 or 41 corresponding to a blowby gas flow ratio smaller than the blowby gas flow ratios acquired at a plurality of points of time, based on the blowby gas flow ratio and an output current of the air-fuel ratio sensor 40 or 41 acquired during fuel cut control at the plurality of points of time of different flows of blowby gas which pass through the blowby gas passage 25 and flow to the downstream side of the throttle valve 18 in the intake passage, and judge abnormality of the air-fuel ratio sensor 40 or 41 based on the calculated output current.

Figure 8:
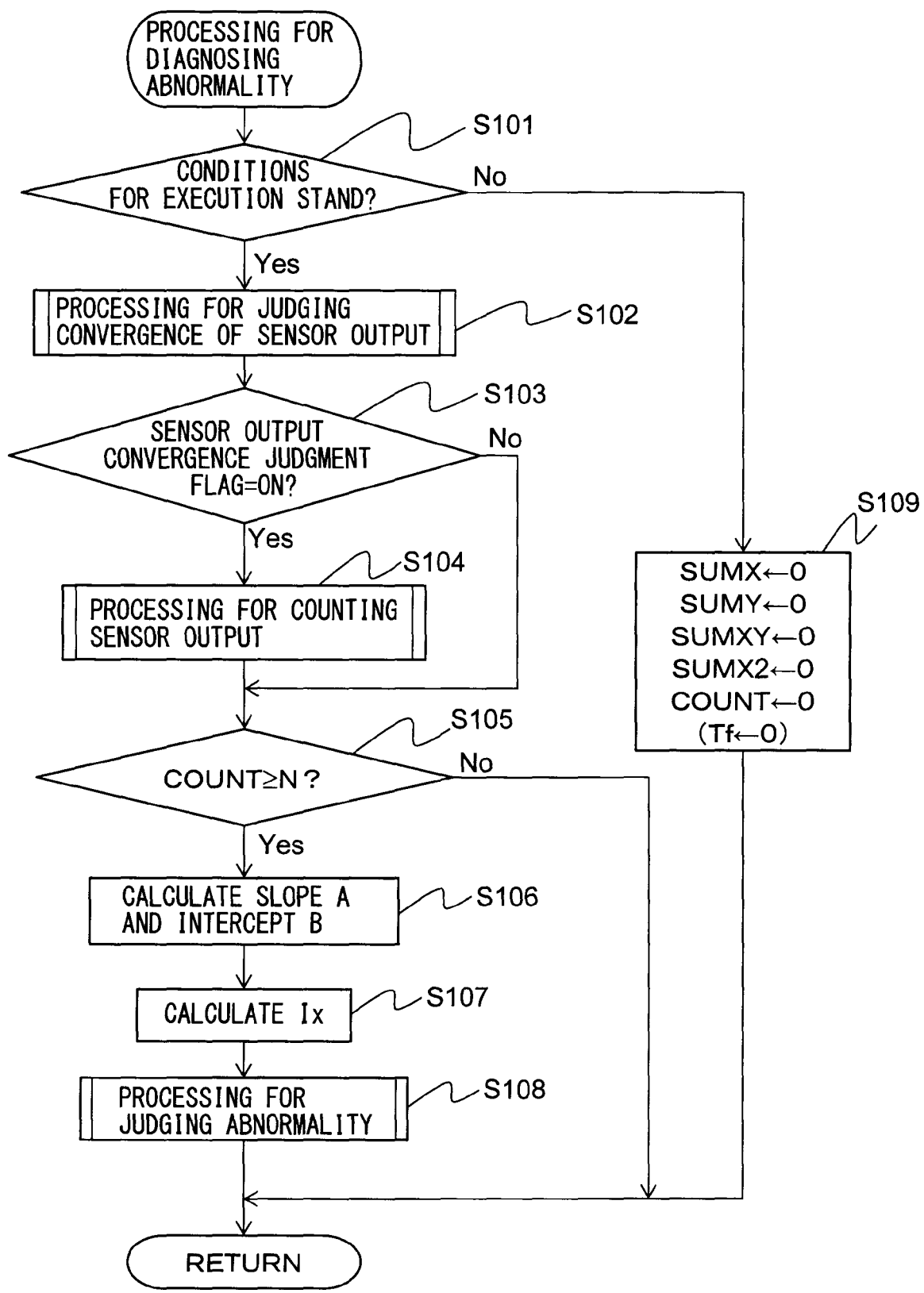
FIG. 8 is a flow chart which shows a control routine for processing for diagnosing abnormality of an air-fuel ratio sensor in a first embodiment of the present invention.

FIG. 8 is a flow chart which shows a control routine for processing for diagnosing abnormality of the air-fuel ratio sensor 40 or 41 in the first embodiment of the present invention. The illustrated control routine is performed by interruption at certain time intervals. In the first embodiment, first, at step S101, it is judged if conditions for execution of processing for diagnosing abnormality stand. The case where the conditions for execution of processing for diagnosing abnormality stand is, for example, the case where fuel cut control is underway and the air-fuel ratio sensor 40 or 41 is active. The case where the air-fuel ratio sensor 40 or 41 is active is the case where the temperature of the sensor element of the air-fuel ratio sensor 40 or 41 is a predetermined value or more, for example, the case where the impedance of the sensor element of the air-fuel ratio sensor 40 or 41 is a predetermined value or less.

When at step S101 it is judged that the conditions for execution of processing for diagnosing abnormality stand, the routine proceeds to step S102. At step S102, the control routine for processing for judging convergence of the sensor output of the air-fuel ratio sensor 40 or 41 is performed. This control routine differs between the upstream side air-fuel ratio sensor 40 and the downstream side air-fuel ratio sensor 41. Note that, the case where, at step S101, it is judged that the conditions for execution of processing for diagnosing abnormality do not stand will be explained later.

First, the control routine for judgment of convergence of sensor output of the downstream side air-fuel ratio sensor 41 will be explained.

Figure 9:
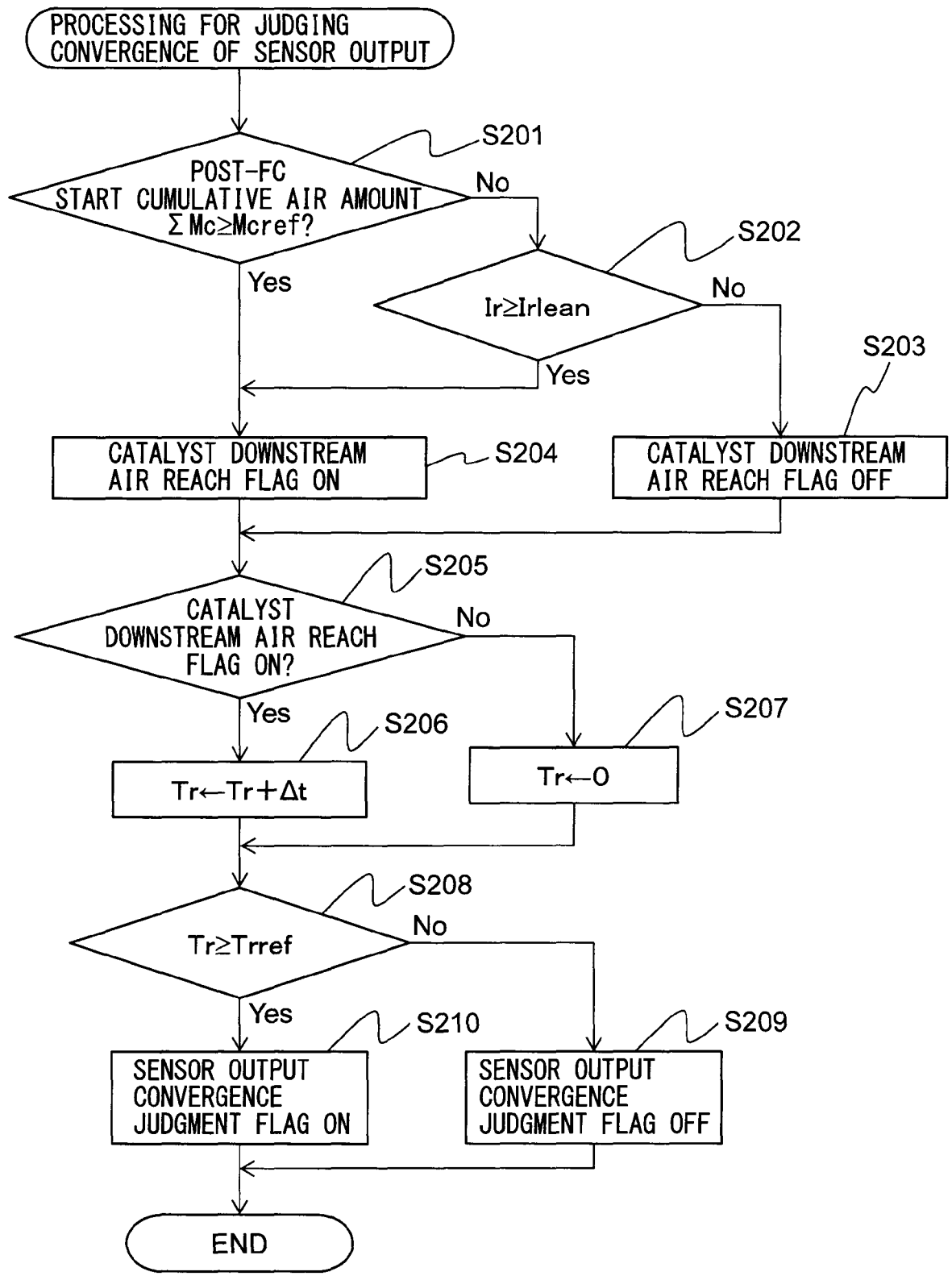
FIG. 9 is a flow chart which shows a control routine for processing for judging convergence of sensor output of a downstream side air-fuel ratio sensor in the first embodiment of the present invention.

FIG. 9 is a flow chart which shows a control routine for processing for judging convergence of sensor output of the downstream side air-fuel ratio sensor 41 in the first embodiment of the present invention. The abnormality diagnosis of the downstream side air-fuel ratio sensor 41 has to be performed after fuel cut control is started and air has reached the downstream side air-fuel ratio sensor 41 at the downstream side of the upstream side exhaust purification catalyst 20 and the sensor output of the downstream side air-fuel ratio sensor 41 has converged. For this reason, the control routine shown in FIG. 9 is used to judge if the sensor output of the downstream side air-fuel ratio sensor 41 has converged.

As shown in FIG. 9, first, at step S201, it is judged if the cumulative value of the amount of intake air (cumulative amount of air) ΣMc fed to a combustion chamber 5 from when fuel cut control is started is a predetermined reference cumulative amount Mcref or more. The cumulative amount of air is, for example, calculated based on the output of the air flowmeter 39. In addition, at step S202, it is judged if the output current Ir of the downstream side air-fuel ratio sensor 41 has become a lean judgment reference value Irlean larger than zero, or more.

If at steps S201 and S202 it is judged that the cumulative amount of air ΣMc after the start of fuel cut control is smaller than a reference cumulative amount Mcref and the output current Ir of the downstream side air-fuel ratio sensor 41 is smaller than the lean judged reference value Irlean, it may be considered that the oxygen storage amount of the upstream side exhaust purification catalyst 20 have not reached the maximum storable oxygen amount Cmax. For this reason, in such a case, the routine proceeds to step S203. At step S203, a catalyst downstream air reach flag is set to OFF and the routine proceeds to step S205.

On the other hand, if at step S201 the cumulative amount of air ΣMc after the start of fuel cut control is the reference cumulative amount Mcref or more or if at step S202 the output current Ir of the downstream side air-fuel ratio sensor 41 is the lean judged reference value Irlean or more, it may be considered that the oxygen storage amount of the upstream side exhaust purification catalyst 20 has reached the maximum storable oxygen amount Cmax. Therefore, after that, the air-fuel ratio of the exhaust gas flowing out from the upstream side exhaust purification catalyst 20 gradually rises. For this reason, in such a case, the routine proceeds to step S204. At step S204, the catalyst downstream air reach flag is set to ON and the routine proceeds to step S205.

At step S205, it is judged if the catalyst downstream air reach flag is ON. If it is judged that the catalyst downstream air reach flag is ON, the routine proceeds to step S206. At step S206, the elapsed time Tr from when air reaches the downstream side of the upstream side exhaust purification catalyst 20 after the start of fuel cut control is calculated. Specifically, the value of the elapsed time Tr plus the slight time Δt (corresponding to interval of execution of control routine) is made the new elapsed time Tr. On the other hand, if at step S205 it is judged that the catalyst downstream air reach flag is OFF, it may be considered that air has not reached the downstream side of the upstream side exhaust purification catalyst 20, and therefore the routine proceeds to step S207 where the elapsed time Tr is reset and made zero.

Next, at step S208, it is judged if the elapsed time Tr is a predetermined convergence judgment reference time Trref or more. If it is judged that the elapsed time Tr is shorter than the convergence judgment reference time Trref, the routine proceeds to step S209. In this case, it may be considered that the output current Ir of the downstream side air-fuel ratio sensor 41 has not converged, and therefore the sensor output convergence judgment flag is set to OFF and, after that, the control routine for processing for judging convergence of sensor output is ended. On the other hand, if it is judged that the elapsed time Tr is the convergence judgment reference time Trref or more, the routine proceeds to step S210. In this case, it may be considered that the output current Ir of the downstream side air-fuel ratio sensor 41 has converged, and therfore the sensor output convergence judgment flag is set to ON and, after that, the control routine for the processing for judging convergence of sensor output is ended.

Next, the control routine for judging convergence of sensor output of the upstream side air-fuel ratio sensor 40 will be explained.

Figure 10:
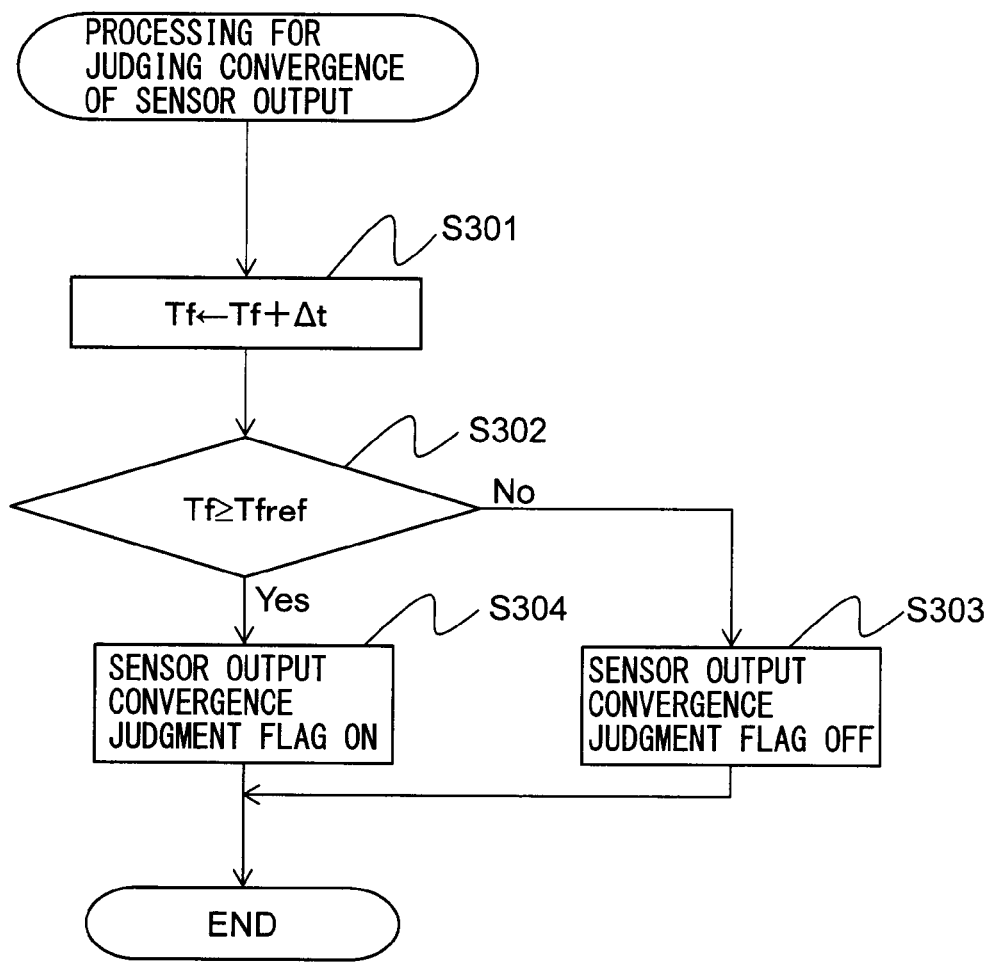
FIG. 10 is a flow chart which shows a control routine for processing for judging convergence of sensor output of an upstream side air-fuel ratio sensor in the first embodiment of the present invention.

FIG. 10 is a flow chart which shows a control routine for processing for judging convergence of sensor output of the upstream side air-fuel ratio sensor 40 in the first embodiment of the present invention. The abnormality diagnosis of the upstream side air-fuel ratio sensor 40 has to be performed after the start of fuel cut control when air reaches the upstream side air-fuel ratio sensor 40 and the sensor output of the upstream side air-fuel ratio sensor 40 converges. For this reason, the control routine shown in FIG. 10 is used to judge if the sensor output of the upstream side air-fuel ratio sensor 40 has converged.

In the case of the upstream side air-fuel ratio sensor 40 positioned at the upstream side of the upstream side exhaust purification catalyst 20, it is not necessary to judge if the oxygen storage amount of the upstream side exhaust purification catalyst 20 has reached the maximum storable oxygen amount. For this reason, as shown in FIG. 10, first, at step S301, the elapsed time Tf after the start of fuel cut control is calculated. Specifically, the value of the elapsed time Tf plus a slight time Δt (corresponding to interval of execution of control routine) is made the new elapsed time Tf.

Next, at step S302, it is judged if the elapsed time Tf is a predetermined convergence judgment reference time Tfref or more. If it is judged that the elapsed time Tf is shorter than the convergence judgment reference time Tfref, the routine proceeds to step S303. In this case, it may be considered that the output current If of the upstream side air-fuel ratio sensor 40 has not converged, and therefore the sensor output convergence judgment flag is set to OFF and, after that, the control routine for the processing for judging convergence of sensor output is ended. On the other hand, if it is judged that the elapsed time Tf is the convergence judgment reference time Tfref or more, the routine proceeds to step S304. In this case, the output current If of the upstream side air-fuel ratio sensor 40 may be considered to have converged, and therefore the sensor output convergence judgment flag is set to ON and, after that, the control routine for the processing for judging convergence of sensor output is ended. Note that, the convergence judgment reference time Tfref may be the same time as the convergence judgment reference time Trref.

Referring again to FIG. 8, after the processing for judging convergence of sensor output is performed at step S102, the routine proceeds to step S103. At step S103, it is judged if the sensor output convergence judgment flag is ON. If it is judged that the sensor output convergence judgment flag is ON, the routine proceeds to step S104. On the other hand, if it is judged that the sensor output convergence judgment flag is OFF, the routine proceeds to step S105.

Figure 11:
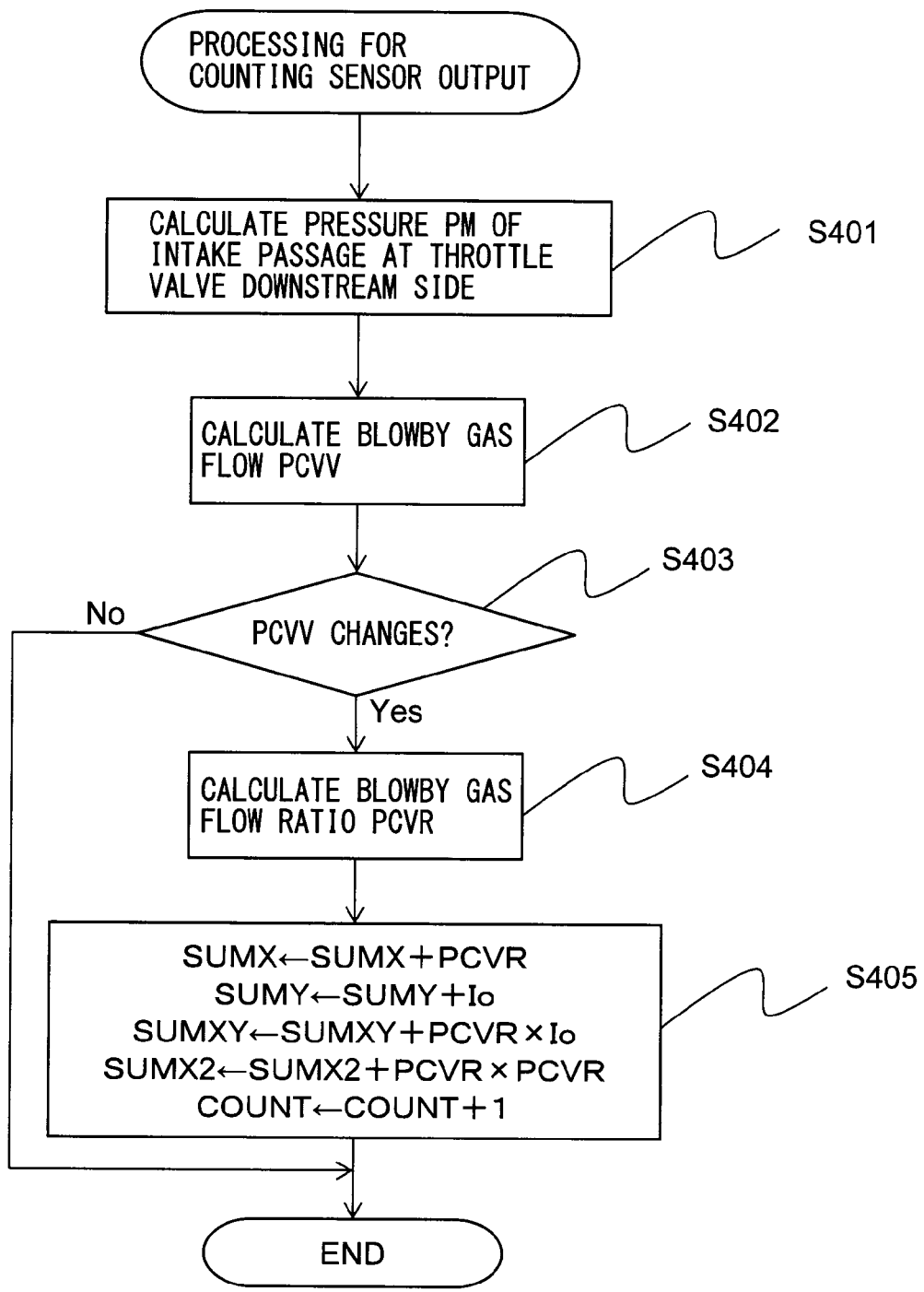
FIG. 11 is a flow chart which shows a control routine for processing for counting sensor output in the first embodiment of the present invention.

At step S104, the control routine for the processing for counting the sensor output shown in FIG. 11 is performed. The control routine for the processing for counting the sensor output will be explained below.

FIG. 11 is a flow chart which shows the control routine for the processing for counting the sensor output in a first embodiment of the present invention. In this control routine, the blowby gas flow ratio and the output current of the air-fuel ratio sensor 40 or 41 are acquired, and the values required for calculating the slope and intercept of the first order approximation line showing the relationship between the blowby gas flow ratio and the output current of the air-fuel ratio sensor 40 or 41 are calculated.

As shown in FIG. 11, first, at step S401, a pressure PM at the downstream side of the throttle valve 18 in the intake passage is calculated. The pressure PM, for example, is directly detected by a pressure sensor provided at the downstream side of the throttle valve 18 in the intake passage or is calculated by known model calculations based on the output of an intake air temperature sensor provided at the downstream side of the throttle valve 18 in the intake passage, the output of the air flowmeter 39, the opening degree of the throttle valve 18, etc.

Next, at step S402, a map which shows the relationship between the pressure PM and a blowby gas flow PCVV is used to calculate the blowby gas flow PCVV based on the pressure PM calculated at step S401. The map is stored in the ROM 34.

Next, at step S403, it is judged if the blowby gas flow PCVV calculated at step S402 has changed from the previously calculated blowby gas flow PCVV. If it is judged that the calculated blowby gas flow PCVV has changed from the previously calculated blowby gas flow PCVV, the routine proceeds to step S404. On the other hand, if it is judged that the calculated blowby gas flow PCVV has not changed from the previously calculated blowby gas flow PCVV, that is, if the calculated blowby gas flow PCVV is the same value as the previously calculated blowby gas flow PCVV, the control routine for processing for counting the sensor output is ended.

Next, at step S404, based on the blowby gas flow PCVV calculated at step S402 and the intake air amount GA taken into a combustion chamber 5 through the throttle valve 18, a blowby gas flow ratio PCVR is calculated by the following equation.

$$PCVR=PCVV/(PCVV+GA)$$

Note that, the intake air amount GA is detected by the air flowmeter 39.

Next, at step S405, a sum SUMX of blowby gas flow ratios PCVR, a sum SUMY of output currents Io of the air-fuel ratio sensor 40 or 41, a sum of products SUMXY of the blowby gas flow ratio PCVR multiplied with the output current Io (below referred to as the "sum of products"), a sum of squares SUMX2 of the blowby gas flow ratio PCVR (below referred to as the "sum of squares"), and the number of times COUNT the control routine for processing for counting the sensor output was executed (below, referred to as "number of times of execution") are calculated.

Specifically, at step S405, the previously calculated sum SUMX of the blowby gas flow ratios PCVR plus the newly calculated blowby gas flow ratio PCVR is made the new sum SUMX of the blowby gas flow ratios PCVR. Further, the previously calculated sum SUMY of the output currents Io plus the newly calculated output current Io is made the new sum SUMY of the output currents Io. Furthermore, the previously calculated sum of products SUMXY plus the product of the newly calculated blowby gas flow PCVV multiplied with the newly detected output current Io is made the new sum of products SUMXY. Further, the previously calculated sum of squares SUMX2 plus the square of the newly calculated blowby gas flow ratio PCVR is made the new sum of squares SUMX2. Furthermore, the previously calculated number of times of execution COUNT plus 1 is made the new number of times of execution COUNT. After that, the control routine for processing for counting the sensor output is ended.

Note that, at step S403 and step S404, instead of the blowby gas flow PCVV calculated at step S402, the blowby gas flow directly detected by a blowby gas flow meter provided at the downstream side (intake runner 13 side) from the PCV valve 26 in the blowby gas passage 25 may be used. In this case, step S401 and step S402 in FIG. 11 are omitted.

Referring again to FIG. 8, after the processing for counting the sensor output is performed at step S104, the routine proceeds to step S105. At step S105, it is judged if the number of times of execution COUNT of the control routine for processing for counting the sensor output is a predetermined value N or more. The predetermined value N is any number of 2 or more. When it is judged that the number of times of execution COUNT is a predetermined value N or more, the routine proceeds to step S106. On the other hand, when it is judged that the number of times of execution COUNT is less than the predetermined value N, the control routine for processing for diagnosing abnormality is ended.

At step S106, based on the values obtained at step S104, the slope A and intercept B of the first order approximation line showing the relationship between the blowby gas flow ratio and the output current of the air-fuel ratio sensor 40 or 41 are calculated by the least square method by the following equations:

$$A=(COUNT \times SUMXY-UMX \times SUMY)/(COUNT \times SUMX2-SUMX \times SUMX)$$

$$B=(SUMX2 \times SUMY-SUMXY \times SUMX)/(COUNT \times SUMX2-SUMX \times SUMX)$$

Next, at step S107, the output current Ix of the air-fuel ratio sensor 40 or 41 corresponding to a blowby gas flow ratio smaller than the blowby gas flow ratios acquired at a plurality of points of time are calculated based on the slope A and intercept B calculated at at step S106, by the following equation:

$$Ix=B+Ax$$

x is made a blowby gas flow ratio which is determined in advance and is smaller than the lower limit value of the blowby gas flow ratios envisioned during fuel cut control.

Figure 12:
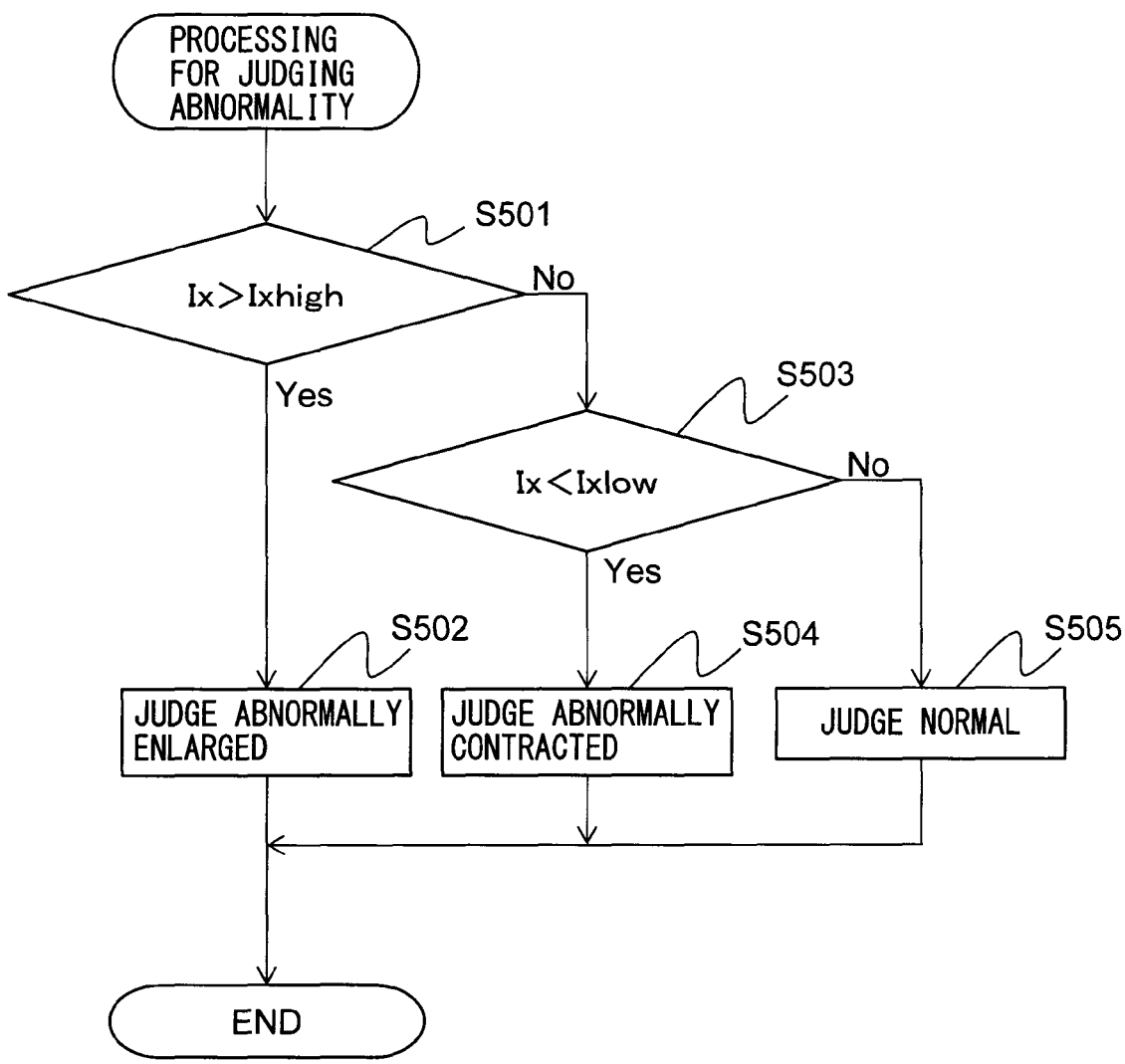
FIG. 12 is a flow chart which shows a control routine for processing for judging abnormality in the first embodiment of the present invention.

Next, at step S108, the control routine for processing for judging abnormality shown in FIG. 12 is performed. The control routine for processing for judging abnormality will be explained below.

FIG. 12 is a flow chart which shows a control routine for processing for judging abnormality in the first embodiment of the present invention. In this control routine, it is judged if the air-fuel ratio sensor 40 or 41 is abnormal, based on the output current Ix calculated at step S107 in FIG. 8.

As shown in FIG. 12, first, at step S501, it is judged if the output current Ix calculated at step S107 in FIG. 8 is larger than a predetermined upper limit current Ixhigh. The upper limit current Ixhigh is, for example, the upper limit value of the output current corresponding to the concentration of oxygen in the air or a current slightly different from this upper limit value.

If at step S501 it is judged that the output current Ix is larger than the upper limit current Ixhigh, the routine proceeds to step S502. At step S502, it is judged that the gain of an air-fuel ratio sensor 40 or 41 is abnormally expanding, and the warning lamp is turned on. After that, the control routine for processing for judging abnormality is ended. On the other hand, if at step S501 it is judged that the output current Ix is the upper limit current Ixhigh or less, the routine proceeds to step S503.

At step S503, it is judged if the output current Ix is less than a predetermined lower limit current Ixlow. The lower limit current Ixlow is, for example, the lower limit value of the output current corresponding to the concentration of oxygen in the air or a current slightly different from this lower limit value.

If at step S503 it is judged that the output current Ix is less than the lower limit current Ixlow, the routine proceeds to step S504. At step S504, it is judged that the gain of the air-fuel ratio sensor 40 or 41 has abnormally contracted, and a warning lamp is turned on. After that, the control routine for processing for judging abnormality is ended. On the other hand, if at step S503 it is judged that the output current Ix is the lower limit current Ixlow or more, the routine proceeds to step S505. At step S505, it is judged that the air-fuel ratio sensor 40 or 41 is normal. After that, the control routine for processing for judging abnormality is ended.

Referring again to FIG. 8, after processing for judging abnormality is performed at step S108, the control routine for processing for diagnosing abnormality is ended.

If at step S101 it is judged that the conditions for execution of processing for diagnosing abnormality do not stand, for example, if fuel cut control is not underway or if the air-fuel ratio sensor 40 or 41 is not active, the routine proceeds to step S109. At step S109, all of the values obtained by the processing for counting the sensor output at step S104 are reset and made zero. In addition to this, if the air-fuel ratio sensor being diagnosed for abnormality is the upstream side air-fuel ratio sensor 40, the elapsed time Tf after the start of fuel cut control used in the processing for judging convergence of sensor output shown in FIG. 10 is reset and made zero.

Therefore, even if the processing for counting the sensor output of step S104 is performed during fuel cut control, if the fuel cut control ends before a number of times of execution COUNT becomes N or more, at step S109, the value obtained by the processing for counting the sensor output is reset and made zero. As a result, in the present embodiment, the blowby gas flow ratio and the output current of the air-fuel ratio sensor 40 or 41 are calculated at a plurality of points of time in a single cycle of fuel cut control rather than being calculated over a plurality of cycles of fuel cut control.

If the processing for diagnosing abnormality is performed over a plurality of cycles of fuel cut control, sometimes the amount of oil in the blowby gas will end up changing during the processing for diagnosing abnormality. If the amount of oil in the blowby gas ends up changing during processing for diagnosing abnormality, it is not possible to accurately calculate the slope and intercept of the first order approximation line which shows the relationship between the blowby gas flow ratio and the output current of the air-fuel ratio sensor 40 or 41 such as shown in FIGS. 7A to 7C. However, in the present embodiment, the blowby gas flow ratio and the output current of the air-fuel ratio sensor 40 or 41 at a plurality of points of time in a single cycle of fuel cut control are calculated, and therefore it is possible to avoid misdiagnosis of abnormality of the air-fuel ratio sensor 40 or 41 due to the amount of oil in the blowby gas ending up changing during processing for diagnosing abnormality, and in turn it is possible to raise the precision of abnormality diagnosis.

Second Embodiment

Next, referring to FIG. 13 and FIG. 14, a second embodiment of the present invention will be explained. The abnormality diagnosis system of the second embodiment is configured to calculate the output current of an air-fuel ratio sensor 40 or 41 corresponding to the zero blowby gas flow ratio, based on the blowby gas flow ratio and output current of the air-fuel ratio sensor 40 or 41 acquired during fuel cut control at a plurality of points of time of different flows of blowby gas which pass through the blowby gas passage 25 and flow to the downstream side of the throttle valve 18 in the intake passage, and to judge abnormality of the air-fuel ratio sensor 40 or 41 based on the calculated output current.

Figure 13:
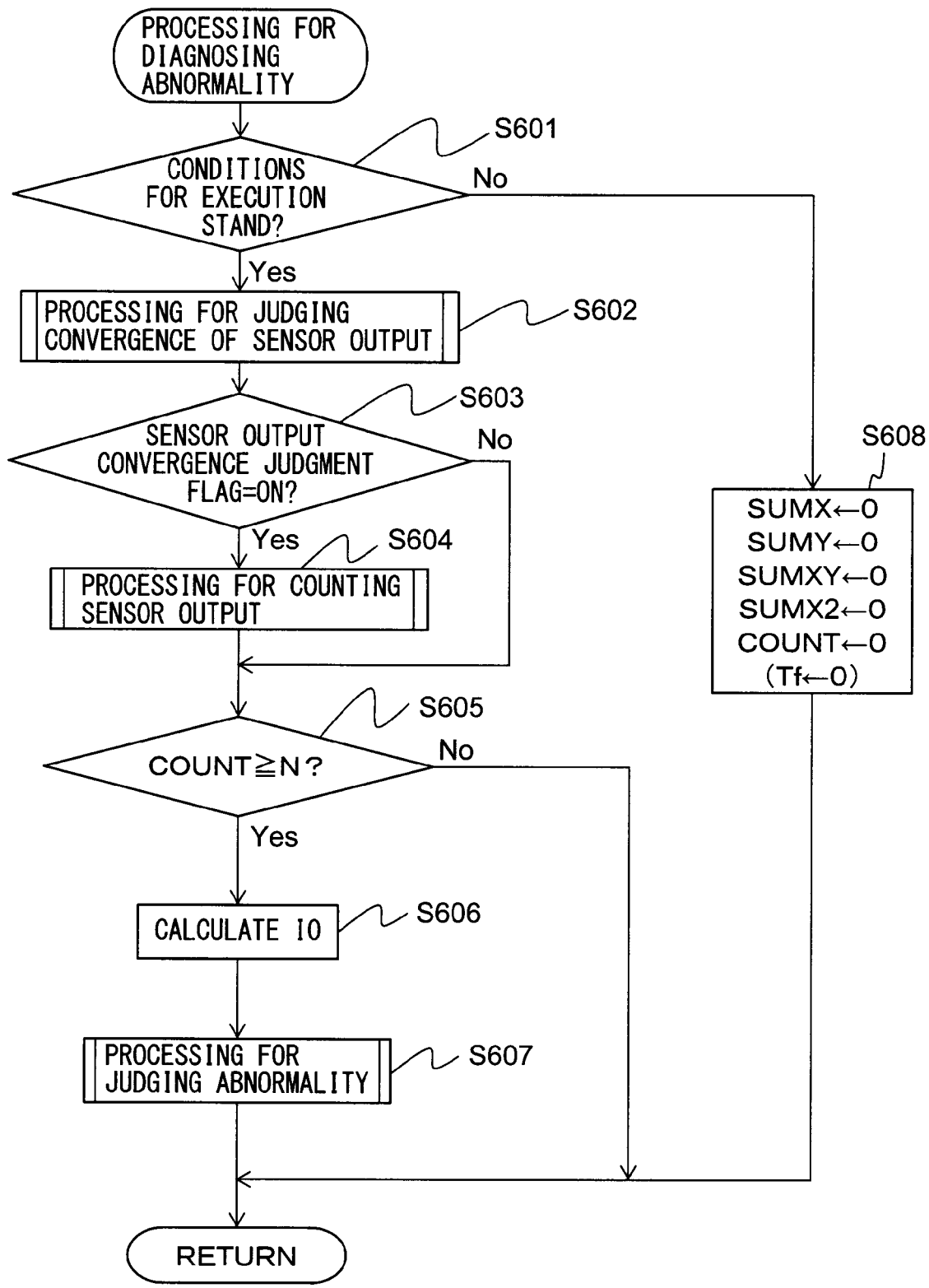
FIG. 13 is a flow chart which shows a control routine for processing for diagnosing abnormality of an air-fuel ratio sensor in a second embodiment of the present invention.

FIG. 13 is a flow chart which shows a control routine for processing for diagnosing abnormality of the air-fuel ratio sensor 40 or 41 in the second embodiment of the present invention. The illustrated control routine is performed by interruption at certain time intervals. Step S601 to step S605 and step S608 in FIG. 13 are similar to step S101 to step S105 and step S109 in FIG. 8, and therefore explanations will be omitted.

At step S606, based on the value obtained at step S604, the output current I0 of the air-fuel ratio sensor 40 or 41 corresponding to a zero blowby gas flow ratio is calculated by the least square method using the following equation:

$$I0=(SUMX2 \times SUMY - SUMXY \times SUMX)/(COUNT \times SUMX2 - SUMX \times SUMX)$$

Note that, the output current I0 of the air-fuel ratio sensor 40 or 41 corresponding to the zero blowby gas flow ratio is equal to the intercept B of the first order approximation line which shows the relationship between the blowby gas flow ratio and the output current of the air-fuel ratio sensor 40 or 41.

Figure 14:
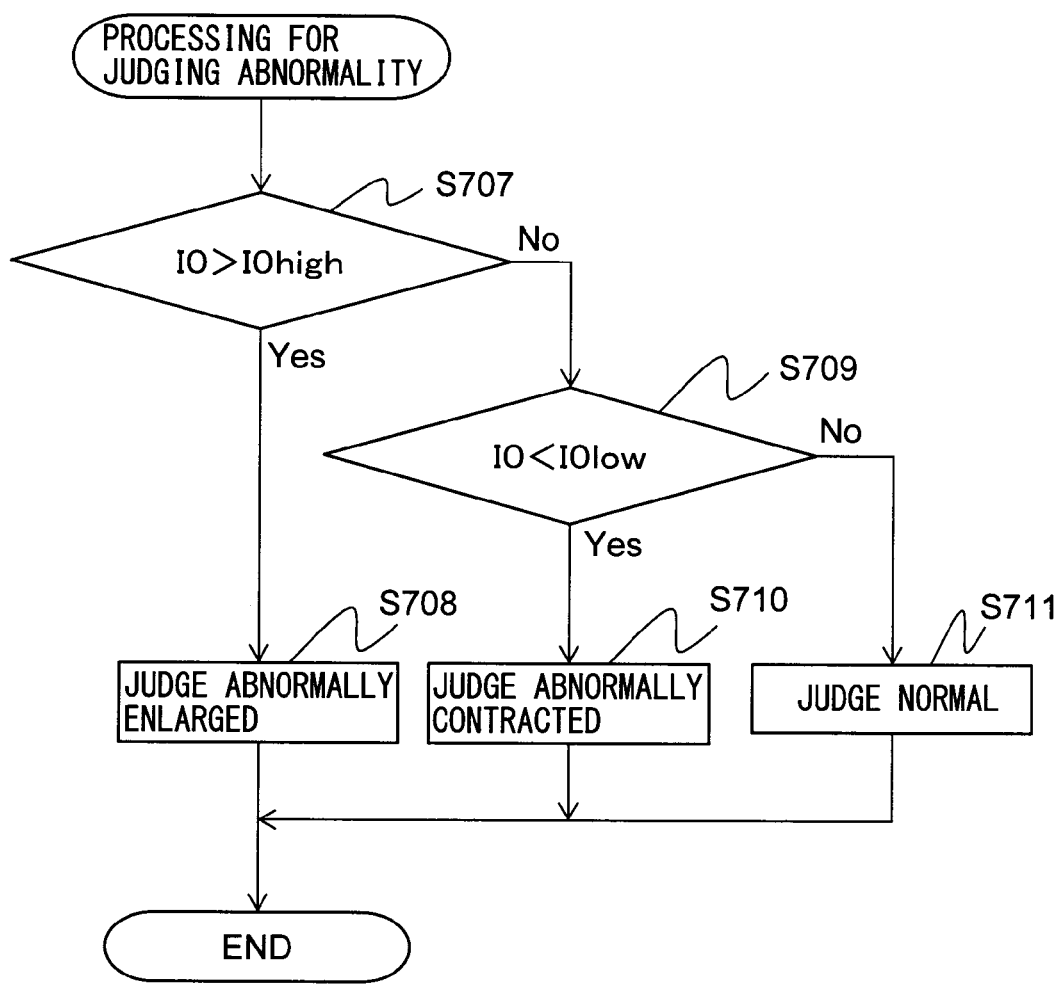
FIG. 14 is a flow chart which shows a control routine for processing for judging abnormality in the second embodiment of the present invention.

Next, at step S607, the control routine for processing for judging abnormality shown in FIG. 14 is performed. The control routine for processing for judging abnormality will be explained below.

FIG. 14 is a flow chart which shows a control routine for processing for judging abnormality in the second embodiment of the present invention. In this control routine, based on the output current I0 calculated at step S606 in FIG. 13, it is judged if the air-fuel ratio sensor 40 or 41 is abnormal.

As shown in FIG. 14, first, at step S707, it is judged if the output current I0 calculated at step S606 is larger than an upper limit current I0high. The upper limit current I0high is made the upper limit value of the output current which is determined in advance and corresponds to the concentration of oxygen in the air or a current slightly different from the upper limit value.

When at step S707 it is judged that the output current I0 is larger than the upper limit current I0high, the routine proceeds to step S708. At step S708, it is judged that the gain of the air-fuel ratio sensor 40 or 41 has abnormally expanded, and a warning lamp is turned on. After that, the control routine for processing for diagnosing abnormality is ended. On the other hand, if at step S707 it is judged that the output current I0 is the upper limit current I0high or less, the routine proceeds to step S709.

At step S709, it is judged if the output current I0 is less than a lower limit current I0low. The lower limit current I0low is made the lower limit value of the output current which is determined in advance and corresponds to the concentration of oxygen in the air or a current slightly different from this lower limit value.

If at step S709 it is judged that the output current I0 is less than the lower limit current I0low, the routine proceeds to step S710. At step S710, it is judged that the gain of the air-fuel ratio sensor 40 or 41 has abnormally contracted, and a warning lamp is turned on. After that, the control routine for processing for diagnosing abnormality is ended. On the other hand, if at step S709 it is judged that the output current I0 is the lower limit current I0low or more, the routine proceeds to step S711. At step S711, it is judged that the air-fuel ratio sensor 40 or 41 is normal. After that, the control routine for processing for diagnosing abnormality is ended.

Third Embodiment

Next, referring to FIG. 15 and FIG. 16, a third embodiment of the present invention will be explained. The abnormality diagnosis system of the third embodiment is configured to calculate the intercept (an output current of air-fuel ratio sensor 40 or 41 corresponding to zero blowby gas flow ratio) of the first order approximation line showing the relationship between the blowby gas flow ratio and the output current of the air-fuel ratio sensor 40 or 41, based on the blowby gas flow ratio and output current of the air-fuel ratio sensor 40 or 41 acquired during fuel cut control at a plurality of points of time of different flows of blowby gas which pass through the blowby gas passage 25 and flow to the downstream side of the throttle valve 18 in the intake passage, calculate the gain (output gain) of the air-fuel ratio sensor 40 or 41 based on the calculated intercept, calculate a rate of change of the calculated gain with respect to a reference value, and judge that the air-fuel ratio sensor 40 or 41 is abnormal when the rate of change is outside a predetermined range.

Figure 15:
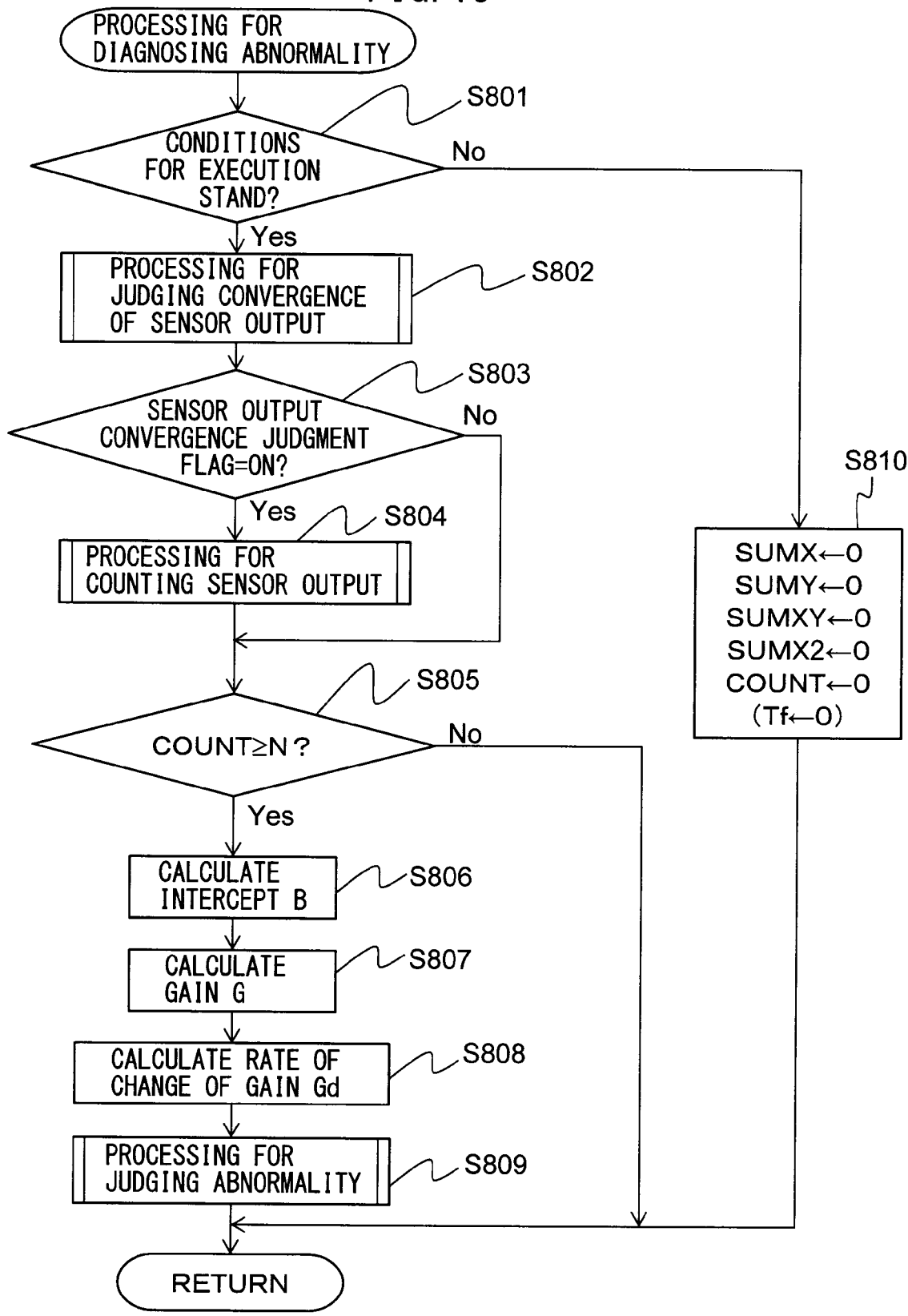
FIG. 15 is a flow chart which shows a control routine for processing for diagnosing abnormality of an air-fuel ratio sensor in a third embodiment of the present invention.

FIG. 15 is a flow chart which shows a control routine for processing for diagnosing abnormality of an air-fuel ratio sensor 40 or 41 in a third embodiment of the present invention. The illustrated control routine is performed by interruption at certain time intervals. Step S801 to step S805 and step S810 in FIG. 15 are similar to step S101 to step S105 and step S109 in the first embodiment in FIG. 8, and therefore explanations will be omitted.

At step S806, based on the values obtained at step S804, the intercept B of the first order approximation line which shows the relationship between the blowby gas flow ratio and the output current of the air-fuel ratio sensor 40 or 41 is calculated by the least square method using the following equation:

$$B = (SUMX2 \times SUMY - SUMXY \times SUMX)/(COUNT \times SUMX2 - SUMX \times SUMX)$$

Next, at step S807, based on the intercept B calculated at step S806, the gain G of the air-fuel ratio sensor 40 or 41 is calculated by the following equation:

$$G = B/Ln(1/0.8)$$

Note that, Ln is a natural log.

The above relationship between the gain G and the intercept B is derived as follows.

First, the output current Ifc of the air-fuel ratio sensor 40 or 41 during fuel cut control is calculated based on the gain G and the concentration O2D_FC of oxygen in the exhaust gas during fuel cut control by the following equation:

$$Ifc = G \times Ln(1/(1-O2D\_FC)) \quad \text{(equation 1)}$$

The concentration O2D_FC of oxygen in the exhaust gas during fuel cut control is calculated based on the concentration of oxygen in the atmosphere, that is, 0.2, and the concentration O2D_C of oxygen consumed by the fuel in the blowby gas by the following equation, since the fuel in the blowby gas consumes oxygen:

$$O2D\_FC = 0.2 - O2D\_C \quad \text{(equation 2)}$$

The concentration O2D_C of oxygen consumed by the fuel in the blowby gas is calculated based on the blowby gas flow ratio PCVR, the concentration FD_B of fuel in the blowby gas, and the concentration K of oxygen consumed per concentration of fuel in the blowby gas by the following equation:

$$O2D\_C = K \times PCVR \times FD\_B \quad \text{(equation 3)}$$

Here, the concentration FD_B of fuel in the blowby gas is calculated based on the oil dilution rate Dilrate and the concentration L of fuel in the blowby gas per oil dilution rate by the following equation:

$$FD\_B = L \times \text{Dilrate} \quad \text{(equation 4)}$$

Note that, the "oil dilution rate" is the value of the amount of fuel mixed into the engine oil divided by the amount of engine oil.

From the above equation 1 to equation 4, the following equation is derived.

$$IL = G \times Ln(1/(0.8 + K \times PCVR \times L \times \text{Dilrate}))$$

Here, if approximating the above equation by a first order equation, the following equation is derived:

$$IL = -G \times K \times L \times \text{Dilrate}/0.8 \times PCVR + G \times Ln(1/0.8)$$

Therefore, the slope A and intercept B of the first order approximation line showing the relationship between the blowby gas flow ratio PCVR and the output current IL of the air-fuel ratio sensor 40 or 41 are expressed by the following equations:

$$A = -G \times K \times L \times \text{Dilrate}/0.8$$

$$B = G \times Ln(1/0.8)$$

Therefore, the gain G is expressed by the following equation.

$$G = B/Ln(1/0.8)$$

Next, at step S808, based on the gain G calculated at step S807, the rate of change of gain Gd with respect to a predetermined reference value Gbase of the gain G is calculated by the following equation:

$$Gd = G/Gbase$$

Figure 16:
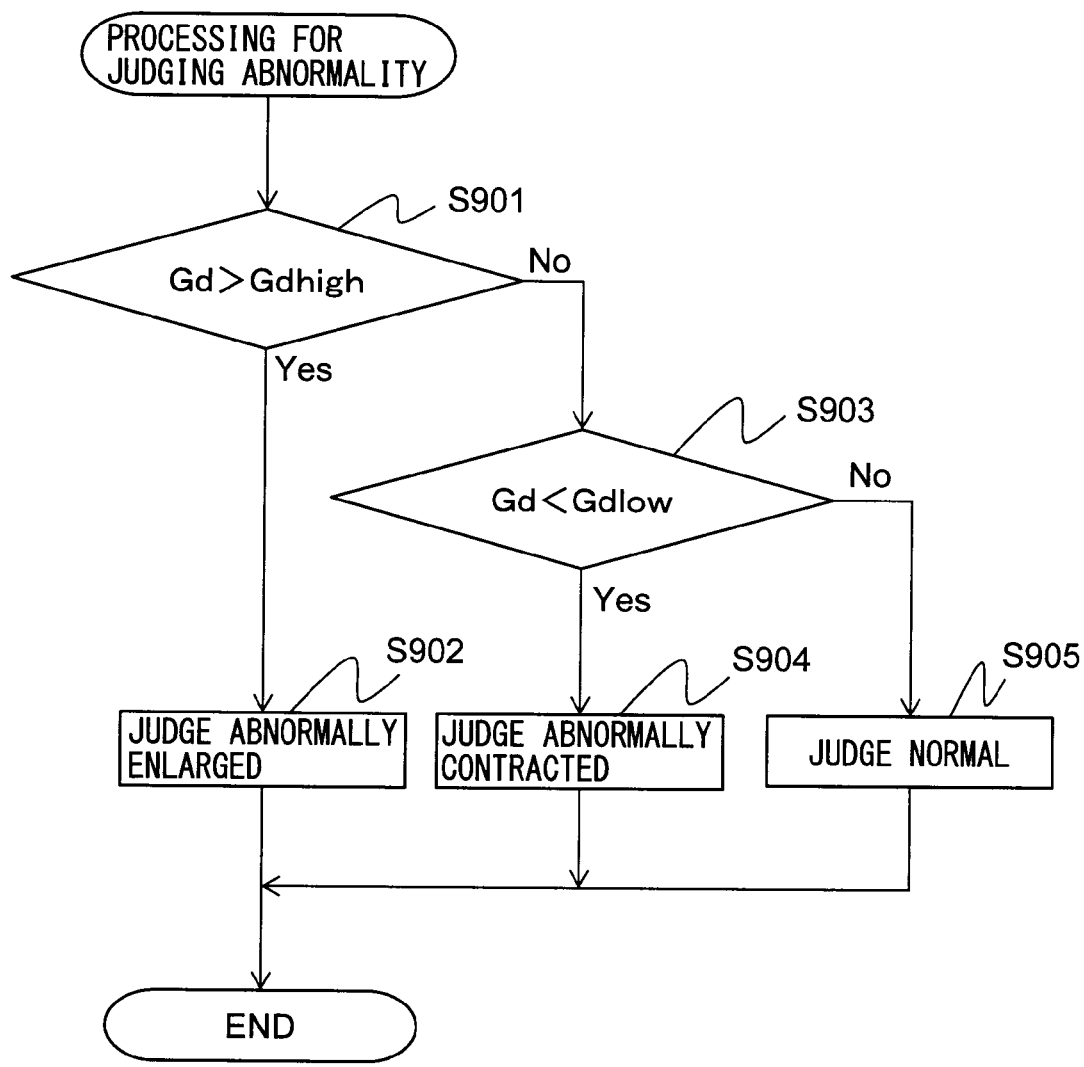
FIG. 16 is a flow chart which shows a control routine for processing for judging abnormality in the third embodiment of the present invention.

Next, at step S809, the control routine for processing for judging abnormality shown in FIG. 16 is performed. The control routine for processing for judging abnormality will be explained below.

FIG. 16 is a flow chart which shows a control routine for processing for judging abnormality in the third embodiment of the present invention. In this control routine, based on the rate of change of gain Gd calculated at step S808 in FIG. 15, it is judged if the air-fuel ratio sensor 40 or 41 is abnormal.

As shown in FIG. 16, first, at step S901, it is judged if the rate of change of gain Gd calculated at step S808 in FIG. 15 is larger than an upper limit rate of change of gain Gdhigh. The upper limit rate of change of gain Gdhigh is made an allowed upper limit value of the rate of change of gain determined in advance or a rate of change of gain slightly different from this upper limit value.

If at step S901 it is judged that the rate of change of gain Gd is larger than the upper limit rate of change of gain Gdhigh, the routine proceeds to step S902. At step S902, it is judged that the gain of the air-fuel ratio sensor 40 or 41 has abnormally expanded, and a warning lamp is turned on. After that, the control routine for processing for diagnosing abnormality is ended. On the other hand, if at step S901 it is judged that the rate of change of gain Gd is the upper limit rate of change of gain Gdhigh or less, the routine proceeds to step S903.

At step S903, it is judged if the rate of change of gain Gd is less than a lower limit rate of change of gain Gdlow. The lower limit rate of change of gain Gdlow is made an allowed lower limit value of the rate of change of gain determined in advance or a rate of change of gain slightly different from this lower limit value.

If at step S903 it is judged that the rate of change of gain Gd is less than the lower limit rate of change of gain Gdlow, the routine proceeds to step S904. At step S904, it is judged that the gain of the air-fuel ratio sensor 40 or 41 has abnormally contracted, and a warning lamp is turned on. After that, the control routine for processing for diagnosing abnormality is ended. On the other hand, if at step S903 it is judged that the rate of change of gain Gd is the lower limit rate of change of gain Gdlow or more, the routine proceeds to step S905. At step S905, it is judged that the air-fuel ratio sensor 40 or 41 is normal. After that, the control routine for processing for diagnosing abnormality is ended.

First Modification of First Embodiment to Third Embodiment

Next, referring to FIG. 17 to FIG. 19, a first modification of the first embodiment to third embodiment of the present invention will be explained. As will be understood from FIG. 7, to accurately calculate the slope and intercept of the first order approximation line showing the relationship between the blowby gas flow ratio and the output current of the air-fuel ratio sensor 40 or 41, it is necessary that the blowby gas flow ratios acquired during fuel cut control are dispersed to a certain extent. For this reason, if the amount of change of the blowby gas flow ratios acquired at a plurality of points of time is small, for example, if the engine speed does not fluctuate that much during fuel cut control, the abnormality diagnosis system cannot accurately calculate the output current of the air-fuel ratio sensor 40 or 41 corresponding to a blowby gas flow ratio smaller than the blowby gas flow ratios acquired at the plurality of points of time, and in turn is liable to not be able to accurately diagnose abnormality of the air-fuel ratio sensor 40 or 41.

Therefore, the abnormality diagnosis system of the first modification of the first embodiment to third embodiment is configured to calculate the amount of change of the blowby gas flow ratios acquired at a plurality of points of time, and to not to judge abnormality of the air-fuel ratio sensor 40 or 41 when the calculated amount of change is less than a predetermined value. As a result, according to the first modification of the first embodiment to third embodiment, it is possible to avoid misdiagnosis of abnormality of the air-fuel ratio sensor 40 or 41 due to the small amount of change of the blowby gas flow ratios acquired at the plurality of points of time, and in turn it is possible to raise the precision of abnormality diagnosis.

Figure 17:
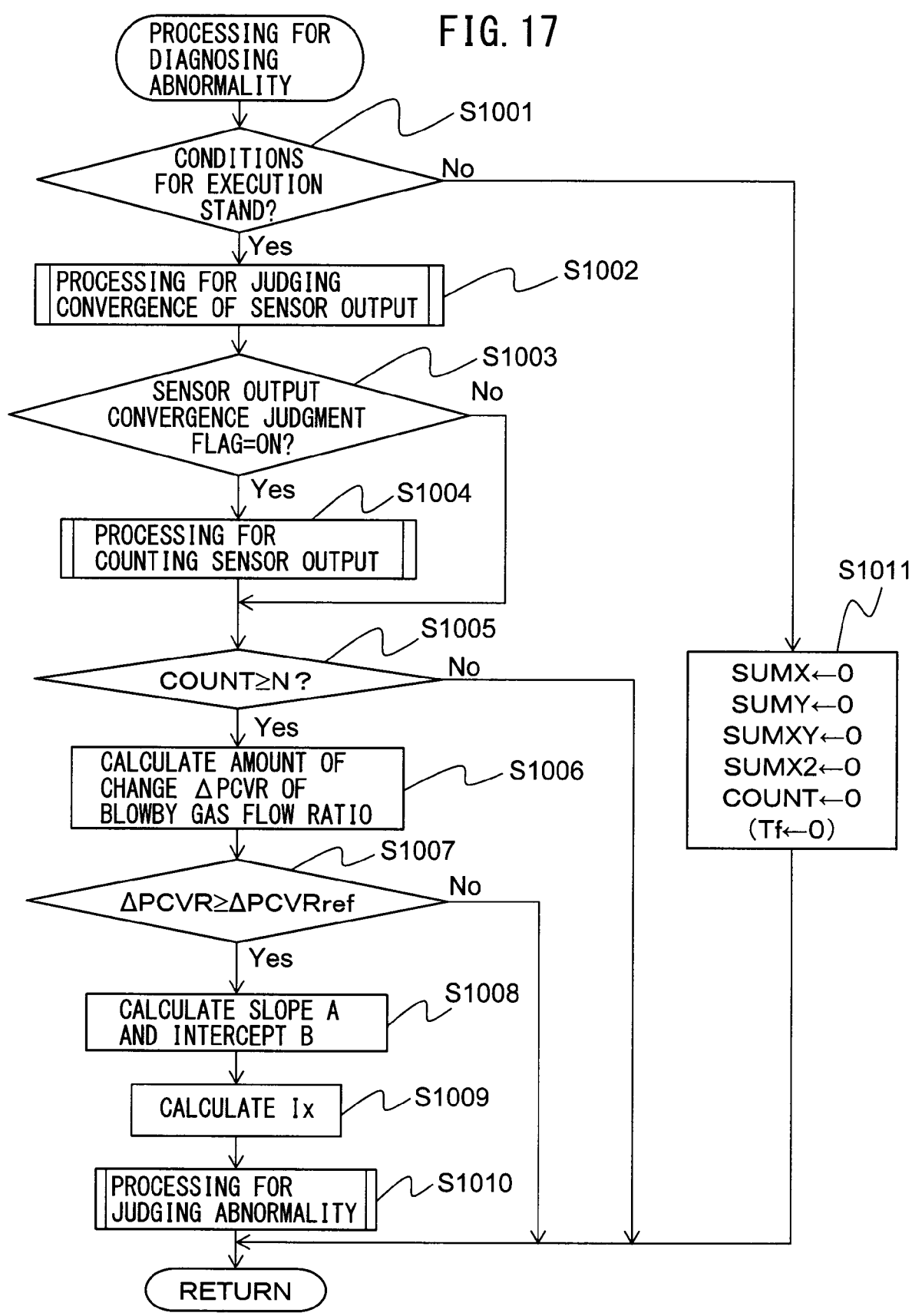
FIG. 17 is a flow chart which shows a control routine for processing for diagnosing abnormality of an air-fuel ratio sensor in a first modification of the first embodiment of the present invention.

FIG. 17 is a flow chart which shows a control routine for processing for diagnosing abnormality of the air-fuel ratio sensor 40 or 41 in a first modification of the first embodiment of the present invention. The illustrated control routine is performed by interruption at certain time intervals.

Step S1001 to step S1005 and step S1008 to step S1011 in FIG. 17 are similar to step S101 to step S105 and step S106 to step S109 in FIG. 8, and therefore explanations will be omitted.

At step S1006, the amount of change ΔPCVR of the blowby gas flow ratio is calculated. The indicator of the amount of change ΔPCVR is, for example, a co-efficient of change PCVRCV of the blowby gas flow ratio.

The coefficient of change PCVRCV of the blowby gas flow ratio is calculated based on the values obtained at step S1004 by the following equation.

$$PCVRCV=SQRT\{(SUMX2-SUMX \times SUMX/COUNT)/(COUNT-1)\}/(SUMX/COUNT)$$

Note that, SQRT indicates the square root.

Next, at step S1007, it is judged if the amount of change ΔPCVR of the blowby gas flow ratio calculated at step S1006 is a predetermined reference amount of change ΔPCVRref of the blowby gas flow ratio or more.

If at step S1007 it is judged that the amount of change ΔPCVR is ΔPCVRref or more, the routine proceeds to step S1008. On the other hand, if at step S1007 it is judged that the amount of change ΔPCVR is less than the reference amount of change ΔPCVRref, accurate abnormality diagnosis of the air-fuel ratio sensor 40 or 41 is difficult, and therefore the control routine for abnormality diagnosis control is ended.

Note that, as an indicator of the amount of change ΔPCVR at step S1006, the difference PCVRD between the maximum value and minimum value of the blowby gas flow ratios may also be used. In this case, at step S1004, instead of the processing for counting the sensor output shown in FIG. 11, the control routine for processing for counting the sensor output shown in FIG. 18 is performed.

Figure 18:
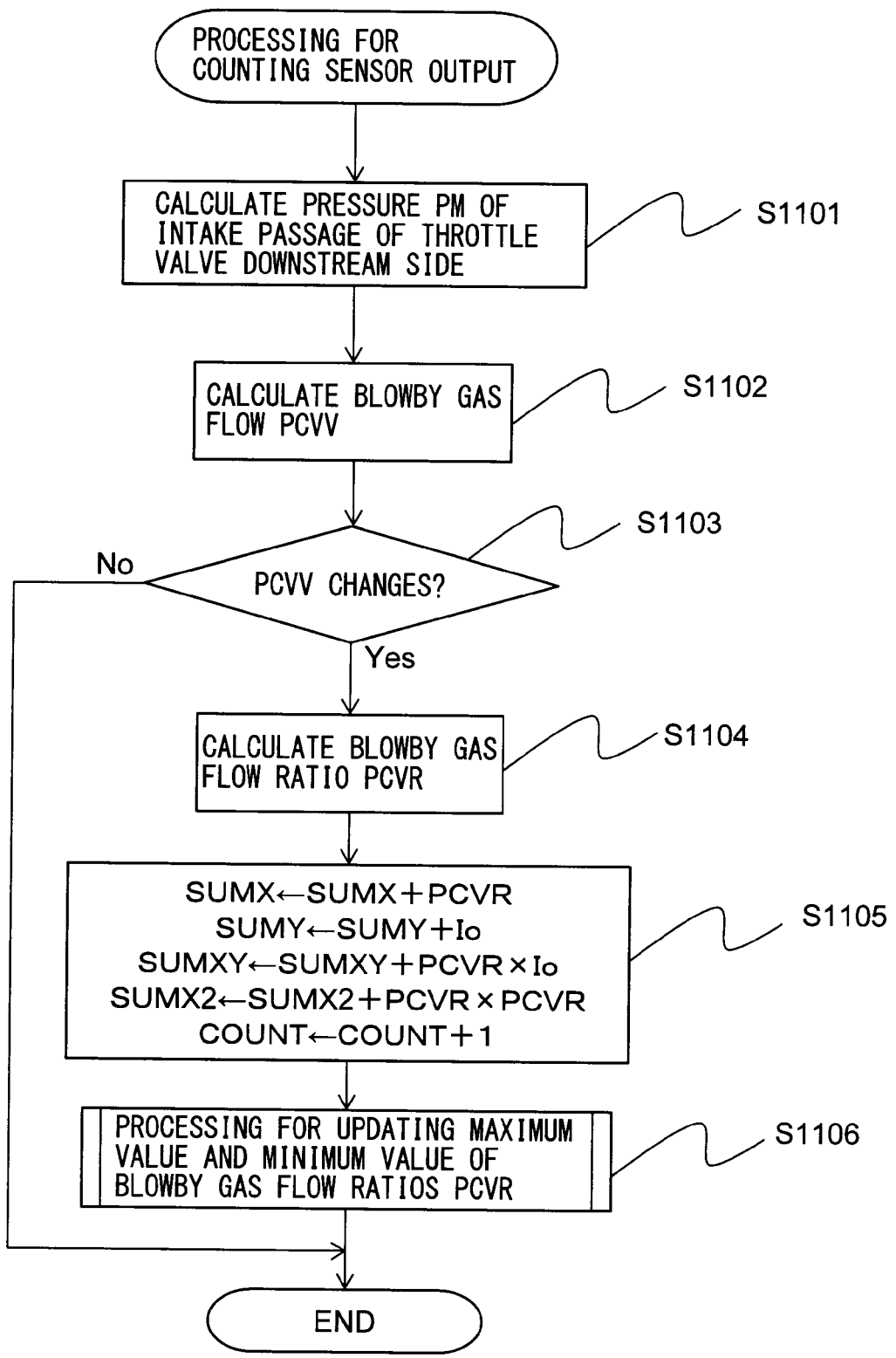
FIG. 18 is a flow chart which shows a control routine for processing for counting sensor output in a first modification of the first embodiment to third embodiment when a difference between a maximum value and minimum value of a blowby gas flow ratio is used as an indicator of an amount of change of the blowby gas flow ratio.

FIG. 18 is a flow chart which shows a control routine for processing for counting the sensor output in a first modification of the first embodiment to third embodiment when the difference PCVRD between the maximum value and minimum value of the blowby gas flow ratios is used as an indicator of the amount of change ΔPCVR. Note that, steps S1101 to S1105 in FIG. 18 are similar to steps S401 to S405 in FIG. 11, and therefore explanations will be omitted. In the control routine for processing for counting the sensor output shown in FIG. 18, the routine proceeds to step S1106 after step S1105. At step S1106, the control routine for processing for updating the maximum value and minimum value of the blowby gas flow ratios PCVR shown in FIG. 19 is performed.

Figure 19:
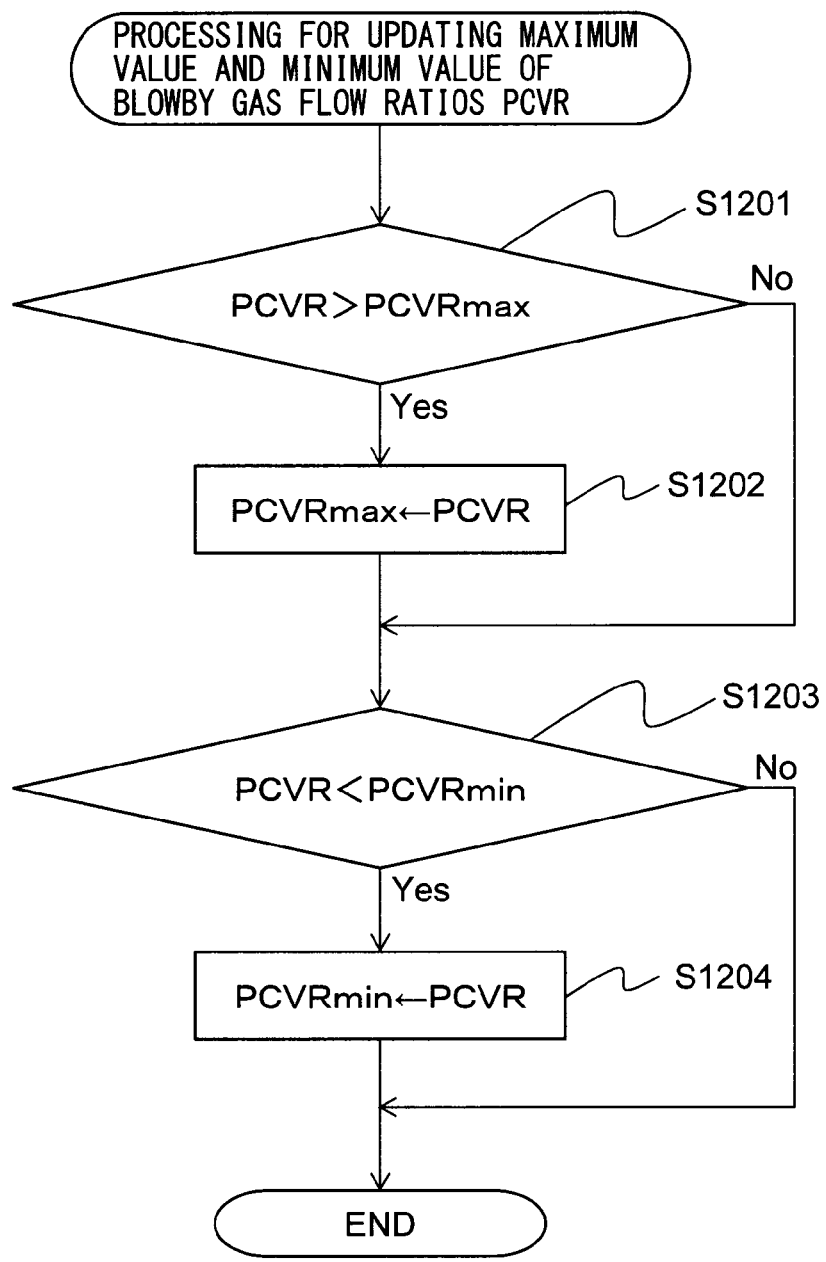
FIG. 19 is a flow chart which shows a control routine for processing for updating a maximum value and minimum value of a blowby gas flow ratio.

FIG. 19 is a flow chart which shows a control routine for processing for updating the maximum value and minimum value of the blowby gas flow ratios PCVR. In this control routine, the blowby gas flow ratio PCVR calculated at step S1104 in FIG. 18 is compared with the maximum value PCVRmax and minimum value PCVRmin of the blowby gas flow ratios calculated at points of time before that, and the maximum value PCVRmax and minimum value PCVRmin of the blowby gas flow ratios are updated.

As shown in FIG. 19, first, at step S1201, it is judged if the blowby gas flow ratio PCVR calculated at step S1104 in FIG. 18 is larger than the maximum value PCVRmax of the blowby gas flow ratios calculated at points of time before that. If it is judged that the blowby gas flow ratio PCVR is larger than the maximum value PCVRmax of the blowby gas flow ratios, the routine proceeds to step S1202. At step S1202, the blowby gas flow ratio PCVR is made the new maximum value PCVRmax of the blowby gas flow ratios and, after that, the routine proceeds to step S1203. On the other hand, if it is judged that the blowby gas flow ratio PCVR is the maximum value PCVRmax of the blowby gas flow ratios or less, the routine proceeds to step S1203 without updating the maximum value PCVRmax of the blowby gas flow ratios.

At step S1203, it is judged if the blowby gas flow ratio PCVR calculated at step S1104 in FIG. 18 is smaller than the minimum value PCVRmin of the blowby gas flow ratios calculated at points of time before that. If it is judged that the blowby gas flow ratio PCVR is smaller than the minimum value PCVRmin of the blowby gas flow ratios, the routine proceeds to step S1204. At step S1204, the blowby gas flow ratio PCVR is made the new minimum value PCVRmin of the blowby gas flow ratios and, after that, the control routine for processing for updating the maximum value and minimum value of the blowby gas flow ratios PCVR is ended. On the other hand, if it is judged that the blowby gas flow ratio PCVR is the minimum value PCVRmin of the blowby gas flow ratios or more, the control routine for processing for updating the maximum value and minimum value of the blowby gas flow ratios PCVR is ended without updating the minimum value PCVRmin of the blowby gas flow ratios.

Referring again to FIG. 18, at step S1106, processing for updating the maximum value and minimum value of the blowby gas flow ratios PCVR is performed, then the control routine for processing for counting the sensor output is ended.

In the same way as the first modification of the first embodiment, in the first modification of the second embodiment, step S1006 and step S1007 in FIG. 17 are performed between step S605 and step S606 in FIG. 13. Further, in the first modification of the third embodiment, step S1006 and step S1007 in FIG. 17 are performed between step S805 and step S806 in FIG. 15.

Second Modification of First Embodiment to Third Embodiment

Next, referring to FIG. 20 to FIG. 22, a second modification of the first embodiment to third embodiment of the present invention will be explained. The gain of the air-fuel ratio sensor 40 or 41 fluctuates depending on the temperature of the sensor element, atmospheric pressure, etc. For this reason, if the temperature of the sensor element, atmospheric pressure, etc. fluctuate while the blowby gas flow ratio and the output current of the air-fuel ratio sensor 40 or 41 are being acquired, the abnormality diagnosis system cannot accurately calculate the output current of the air-fuel ratio sensor 40 or 41 corresponding to a blowby gas flow ratio smaller than the blowby gas flow ratios acquired at a plurality of points of time, and in turn abnormality of the air-fuel ratio sensor 40 or 41 is liable to be unable to be accurately diagnosed.

Therefore, the abnormality diagnosis system of the second modification of the first embodiment to third embodiment is configured to further acquire values of variation factors which cause the output current of the air-fuel ratio sensor 40 or 41 to fluctuate, for example, the impedance of the sensor element and the atmospheric pressure, at the plurality of points of time when the blowby gas flow ratio and output current of the air-fuel ratio sensor 40 or 41 are acquired, calculate the amounts of change of the values of the variation factors acquired, and not judge abnormality of the air-fuel ratio sensor 40 or 41 when the calculated amounts of change are predetermined values or more. As a result, according to the second modification of the first embodiment to third embodiment, it is possible to avoid misdiagnosis of abnormality of the air-fuel ratio sensor 40 or 41 caused by fluctuation of the variation factors which cause fluctuation of the output current of the air-fuel ratio sensor 40 or 41 in the period while acquiring the blowby gas flow ratio and output current of the air-fuel ratio sensor 40 or 41, and in turn it is possible to raise the precision of abnormality diagnosis.

Figure 20:
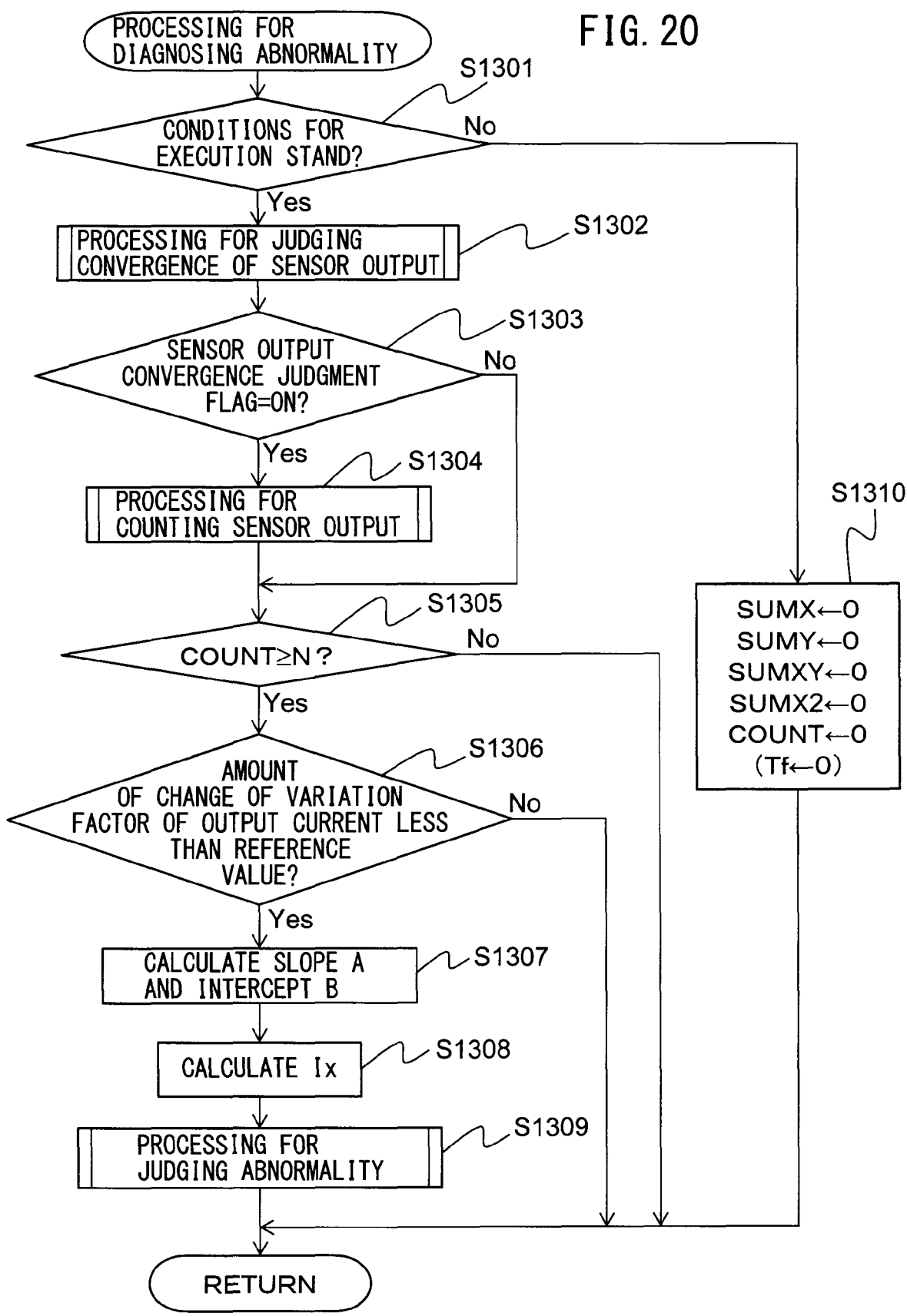
FIG. 20 is a flow chart which shows a control routine for processing for diagnosing abnormality of an air-fuel ratio sensor in a second modification of the first embodiment of the present invention.

FIG. 20 is a flow chart which shows a control routine for processing for diagnosing abnormality of the air-fuel ratio sensor 40 or 41 in a second modification of the first embodiment of the present invention. The illustrated control routine is performed by interruption at certain time intervals.

Step S1301 to step S1303, step S1305, and step S1307 to step S1310 in FIG. 20 are similar to step S101 to step S103, step S105, and step S106 to step S109 in FIG. 8, and therefore explanations will be omitted.

Figure 21:
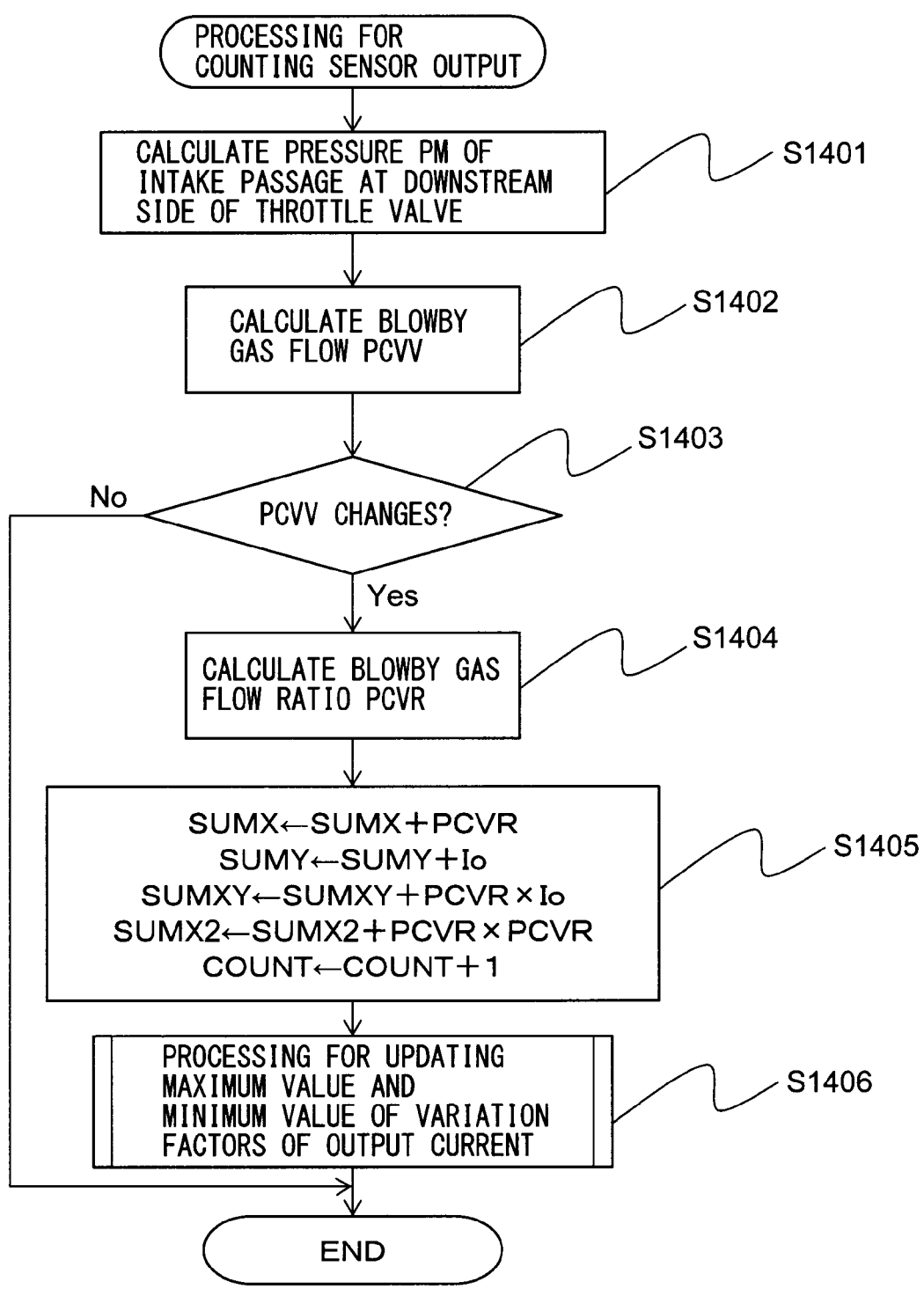
FIG. 21 is a flow chart which shows a control routine for processing for counting sensor output in a second modification of the first embodiment to third embodiment of the present invention.

At step S1304, the control routine for processing for counting the sensor output shown in FIG. 21 is executed. FIG. 21 is a flow chart which shows a control routine for processing for counting the sensor output in the second modification of the first embodiment to third embodiment. Note that, steps S1401 to S1405 in FIG. 21 are similar to steps S401 to S405 in FIG. 11, and therefore explanations will be omitted.

In the control routine for processing for counting the sensor output shown in FIG. 21, the routine proceeds to step S1406 after step S1405. At step S1406, the control routine for processing for updating the maximum values and minimum values of the variation factors of the output current in FIG. 22 is performed.

FIG. 22 is a flow chart which shows a control routine for processing for updating the maximum values and minimum values of the variation factors of the output current. In this control routine, the variation factors of the output current, that is, the sensor element impedance IP and atmospheric pressure P, are acquired, the acquired sensor element impedance IP and atmospheric pressure P are respectively compared with the maximum value IPmax and minimum value IPmin of the sensor element impedances and maximum value Pmax and minimum value Pmin of the atmospheric pressures calculated at points of time before that, and the maximum value IPmax and minimum value IPmin of the sensor element impedances and maximum value Pmax and minimum value Pmin of the atmospheric pressures are updated.

As shown in FIG. 22, first, at step S1501, the sensor element impedance IP is acquired, and it is judged if the acquired sensor element impedance IP is larger than the maximum value IPmax of the sensor element impedances acquired at points of time before that. If it is judged that the sensor element impedance IP is larger than the maximum value IPmax of the sensor element impedances, the routine proceeds to step S1502. At step S1502, the sensor element impedance IP is made the new maximum value IPmax of the sensor element impedances and, after that, the routine proceeds to step S1503. On the other hand, if it is judged that the sensor element impedance IP is the maximum value IPmax of the sensor element impedances or less, the routine proceeds to step S1503 without updating the maximum value IPmax of the sensor element impedances.

At step S1503, it is judged if the acquired sensor element impedance IP is smaller than the minimum value IPmin of the sensor element impedances acquired at points of time before that. If it is judged that the sensor element impedance IP is smaller than the minimum value IPmin of the sensor element impedances, the routine proceeds to step S1504. At step S1504, the sensor element impedance IP is made the new minimum value IPmin of the sensor element impedances and, after that, the routine proceeds to step S1505. On the other hand, if it is judged that the sensor element impedance IP is the minimum value IPmin of the sensor element impedances or more, the routine proceeds to step S1505 without updating the minimum value IPmin of the sensor element impedances.

At step S1505, the atmospheric pressure P is acquired, and it is judged if the acquired atmospheric pressure P is larger than the maximum value Pmax of the atmospheric pressures acquired at points of time before that. If it is judged that the atmospheric pressure P is larger than the maximum value Pmax of the atmospheric pressures, the routine proceeds to step S1506. At step S1506, the atmospheric pressure P is made the new maximum value Pmax of the atmospheric pressures and, after that, the routine proceeds to step S1507. On the other hand, if it is judged that the atmospheric pressure P is the maximum value Pmax of the atmospheric pressures or less, the routine proceeds to step S1507 without updating the maximum value Pmax of the atmospheric pressures.

At step S1507, it is judged if the acquired atmospheric pressure P is smaller than the minimum value Pmin of the atmospheric pressures acquired at points of time before that. If it is judged that the atmospheric pressure P is smaller than the minimum value Pmin of the atmospheric pressures, the routine proceeds to step S1508. At step S1508, the atmospheric pressure P is made the new minimum value Pmin of the atmospheric pressures and, after that, the control routine for processing for updating the maximum values and minimum values of the variation factors of the output current is ended. On the other hand, if it is judged that the atmospheric pressure P is the minimum value Pmin of the atmospheric pressures or more, the control routine for processing for updating the maximum values and minimum values of the variation factors of the output current is ended without updating the minimum value Pmin of the atmospheric pressures.

Referring again to FIG. 21, at step S1406, the processing for updating the maximum values and minimum values of the variation factors of the output current is performed, then the control routine for processing for counting the sensor output is ended.

Referring again to FIG. 20, at step S1306, it is judged if the amounts of change of variation factors of the output current is less than predetermined reference amounts of change of the variation factors of the output current. Specifically, for example, based on the maximum value IPmax and minimum value IPmin of the sensor element impedances and the maximum value Pmax and minimum value Pmin of the atmospheric pressures obtained at step S1304, it is judged if the difference between the maximum value IPmax and minimum value IPmin of the sensor element impedances is less than the reference amount of change of the sensor element impedance and the difference between the maximum value Pmax and minimum value Pmin of the atmospheric pressures is less than the reference amount of change of the atmospheric pressure. Alternatively, it may be judged if the value of the difference between the maximum value IPmax and minimum value IPmin of the sensor element impedances multiplied with the difference between the maximum value Pmax and minimum value Pmin of the atmospheric pressures is less than a reference value.

If at step S1306 it is judged that the amounts of change of variation factors of the output current are less than the predetermined reference amounts of change of the variation factors of output current, the routine proceeds to step S1307. On the other hand, if at step S1306 it is judged that the amounts of change of variation factors of the output current are the predetermined reference amounts of change of the variation factors of output current or more, accurate abnormality diagnosis of the air-fuel ratio sensor 40 or 41 is difficult, and therefore the control routine of abnormality diagnosis control is ended.

In the same way as the second modification of the first embodiment, in the second modification of the second embodiment, at step S604 in FIG. 13, instead of the processing for counting the sensor output shown in FIG. 11, the control routine for processing for counting the sensor output shown in FIG. 21 is performed. Step S1306 in FIG. 20 is performed between step S605 and step S606 in FIG. 13. Further, in the second modification of the third embodiment, at step S804 in FIG. 15, instead of the processing for counting the sensor output shown in FIG. 11, the control routine for processing for counting the sensor output shown in FIG. 21 is performed. Step S1306 in FIG. 20 is performed between step S805 and step S806 in FIG. 15.

Note that, in all of the above embodiments, the blowby gas flow ratio and the output current of the air-fuel ratio sensor 40 or 41 may also be calculated not at a plurality of points of time in a single cycle of fuel cut control, but at a plurality of points of time at a plurality of cycles of fuel cut control. In this case, the value obtained by the processing for counting the sensor output is reset and made zero after the end of the processing for judging abnormality instead of being reset and made zero when it is judged that the conditions for execution of processing for diagnosing abnormality do not stand.

Further, if processing for diagnosing abnormality is performed over a plurality of cycles of fuel cut control in such a way, abnormality diagnosis of the air-fuel ratio sensor 40 or 41 may be judged only when the cumulative amount of air in the plurality of cycles of fuel cut control is a predetermined value or less. If the cumulative amount of air in the plurality of cycles of fuel cut control is the predetermined value or less, it is expected that there will be little change in the amount of oil in the blowby gas in the plurality of cycles of fuel cut control. Therefore, by setting the above condition, it is possible to raise the precision of abnormality diagnosis when processing for diagnosing abnormality is performed over a plurality of cycles of fuel cut control.

REFERENCE SIGNS LIST 1. engine body
5. combustion chamber
7. intake port
9. exhaust port
13. intake runner
14. surge tank
18. throttle valve
19. exhaust manifold
20. upstream side exhaust purification catalyst
24. downstream side exhaust purification catalyst
25. blowby gas passage
26. PCV valve
31. ECU
40. upstream side air-fuel ratio sensor
41. downstream side air-fuel ratio sensor

What is claimed is:
1. An abnormality diagnosis system of an air-fuel ratio sensor provided in an internal combustion engine, wherein the internal combustion engine comprises
an intake passage in which a throttle valve is arranged and which leads an air-fuel mixture containing air and fuel to a combustion chamber, an exhaust passage discharging exhaust gas produced by combustion of the air-fuel mixture in the combustion chamber, and a blowby gas passage returning blowby gas in a crankcase to a downstream side of the throttle valve in the intake passage, and the air-fuel ratio sensor is provided in the exhaust passage and detects an air-fuel ratio of the exhaust gas flowing through the exhaust passage, the abnormality diagnosis system comprises an electronic control unit (ECU) comprising a random access memory (RAM), a read only memory (ROM), and a microprocessor (CPU), and performs an abnormality diagnosis of the air-fuel ratio sensor during a fuel cut control in which the internal combustion engine stops feeding fuel to the combustion chamber, wherein the ECU is configured to detect or calculate a pressure at the downstream side of the throttle valve in the intake passage, and calculate a flow of the blowby gas passing through the blowby gas passage and flowing to the downstream side of the throttle valve in the intake passage based on the detected or calculated pressure, acquire a blowby gas flow ratio showing a ratio of the flow of the blowby gas to a total of the flow of the blowby gas and an intake air amount, and an output current of the air-fuel ratio sensor during the fuel cut control at each of a plurality of points of time of different flows of the blowby gas, and calculate another output current of the air-fuel ratio sensor corresponding to another blowby gas flow ratio smaller than the blowby gas flow ratios acquired at the plurality of points of time, by approximating a relationship between the blowby gas flow ratios and the output currents acquired at the plurality of points of time by a linear approximation, and judge an output current abnormality of the air-fuel ratio sensor based on the calculated another output current.

2. The abnormality diagnosis system of an air-fuel ratio sensor according to claim 1, wherein the plurality of points of time are a plurality of points of time at a single cycle of fuel cut control.

3. The abnormality diagnosis system of an air-fuel ratio sensor according to claim 1, wherein the another blowby gas flow ratio smaller than the blowby gas flow ratios acquired at the plurality of points of time is zero.

4. The abnormality diagnosis system of an air-fuel ratio sensor according to claim 1, wherein the abnormality diagnosis system is configured to calculate an output gain of the air-fuel ratio sensor based on the output currents acquired at the plurality of points of time, and calculate a rate of change of the calculated output gain with respect to a reference value, and judge that the air-fuel ratio sensor is abnormal when the rate of change is outside a predetermined range.

5. The abnormality diagnosis system of an air-fuel ratio sensor according to claim 1, wherein the abnormality diagnosis system is configured to calculate an amount of change of the blowby gas flow ratios acquired at the plurality of points of time, and not to judge abnormality of the air-fuel ratio sensor when the amount of change is less than a predetermined value.

6. The abnormality diagnosis system of an air-fuel ratio sensor according to claim 1, wherein the abnormality diagnosis system is configured to acquire values of a variation factor causing the output current of the air-fuel ratio sensor to fluctuate, other than the air-fuel ratio of the exhaust gas, at the plurality of points of time, calculate an amount of change of the values of the variation factor, and not to judge abnormality of the air-fuel ratio sensor when the amount of change is a predetermined value or more.

* * * * *